United States Patent [19]

Takemoto et al.

[11] 4,339,442

[45] Jul. 13, 1982

[54] GYNOSAPONINS, THEIR USE AND A PROCESS FOR PREPARING THE SAME

[76] Inventors: Tsunematsu Takemoto, 36-5, Shimonakasu, Nishisuga-cho, Tokushima; Shigeru Arichi, 1-1002, 6, Terauchi 2-chome, Toyonaka, Osaka; Shigenobu Arihara, 157-1, Jyoryo, Jyoroku-cho, Tokushima; Tadashi Nakajima, 12-9-110, Hirata 2-chome, Ibaraki; Megumi Okuhira, 3-34-403, Wakayamadai 2-chome, Shimamoto-cho, Mishima-gun, Osaka; Yoshihiro Uchida, 22-23, Izuo 1-chome, Taisho-ku, Osaka, all of Japan

[21] Appl. No.: 205,377

[22] Filed: Nov. 7, 1980

[30] Foreign Application Priority Data

| Mar. 11, 1980 | [JP] | Japan | 55-30635 |
| Mar. 11, 1980 | [JP] | Japan | 55-30636 |
| May 8, 1980 | [JP] | Japan | 55-61507 |
| May 8, 1980 | [JP] | Japan | 55-61508 |
| May 8, 1980 | [JP] | Japan | 55-61509 |
| Sep. 27, 1980 | [JP] | Japan | 55-134684 |

[51] Int. Cl.³ .................. A01N 31/00; C07G 3/00
[52] U.S. Cl. .................. 424/182; 536/4.1; 536/5; 435/52
[58] Field of Search .................. 536/4, 5; 424/182

[56] References Cited

U.S. PATENT DOCUMENTS 4,084,010  4/1978  Takemoto et al. .................. 536/5

Primary Examiner—Elbert L. Roberts
Attorney, Agent, or Firm—Hubbell, Cohen, Stiefel & Gross

[57] ABSTRACT

There disclose a group of new saponins designated as gynosaponins which have been isolated from a plant of Gynostemma pentaphyllum Makino of Cucurbitaceae, pharmaceutical use thereof and a method for isolating gynosaponins.

70 Claims, No Drawings

GYNOSAPONINS, THEIR USE AND A PROCESS FOR PREPARING THE SAME

BACKGROUND OF THE INVENTION

1. Field of the Invention

This invention relates to novel saponins which can be isolated from "AMACHAZURU" in Japanese, *Gynostemma pentaphyllum* Makino belonging to Cucurbitaceae, their use and a method for preparing the same.

2. Description of the Prior Art

It is known that some plants such as Panax ginseng and the like contain saponins. Nagai et al report that *Gynostemma pentaphyllum* contains a saponin, whose acid hydrolysis gives panaxadiol as a sapogenin [cf. The 23rd Meeting (1976) of Pharmacognosy Society in Japan]. Also, M. Takemoto et al present that an enzymatic hydrolysis of a saponin extracted from the above plant gives Compound K which is a prosapogenin of a saponin isolated from Panax ginseng [cf. The 24th Meeting (1977) of Pharmacognosy Society in Japan].

The inventors of the present invention have isolated a mixture of saponins in substantially pure form as well as a group of new saponins in individual form, from *Gynostemma pentaphyllum*, and also have found that the saponins possess unique pharmacological activities.

SUMMARY OF THE INVENTION

According to the present invention, it provides gynosaponins represented by the following formula (I) and their non-toxic salts.

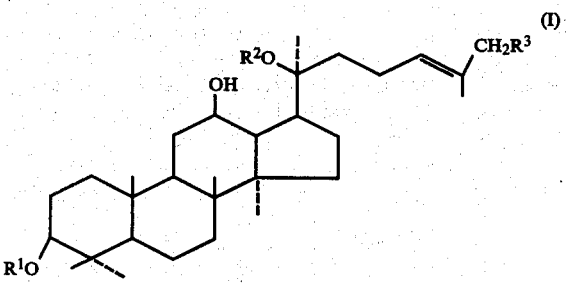

(I)

In the formula (I), (a) when $R^1$ is [β-D-glucopyranosyl (1→2)-α-L-rhamnopyranosyl (1→6)]-β-D-glucopyranosyl group, $R^2$ is hydrogen, β-D-glucopyranosyl (1→6)-β-D-glucopyranosyl group, α-L-rhamnopyranosyl (1→6)-β-D-glucopyranosyl group or β-D-glucopyranosyl group and $R^3$ is hydrogen atom or hydroxy group;

(b) when $R^1$ is β-D-glucopyranosyl (1→2)-β-D-glucopyranosyl group, $R^2$ is α-L-rhamnopyranosyl (1→6)-β-D-glucopyranosyl group and $R^3$ is hydrogen atom or hydroxy group;

(c) when $R^1$ is α-L-rhamnopyranosyl (1→6)-β-D-glucopyranosyl group, $R^2$ is β-D-glucopyranosyl (1→6)-β-D-glucopyranosyl group, α-L-rhamnopyranosyl (1→6)-β-D-glucopyranosyl or β-D-glucopyranosyl group and $R^3$ is hydrogen atom;

(d) when $R^1$ is D-glucopyranosyl group, $R^2$ is β-D-xylopyranosyl (1→6)-β-D-glucopyranosyl, α-L-rhamnopyranosyl (1→6)-β-D-glucopyranosyl or β-D-glucopyranosyl (1→6)-β-D-glucopyranosyl group and $R^3$ is hydrogen atom;

(e) when $R^1$ is hydrogen atom, $R^2$ is β-D-glucopyranosyl, β-D-xylopyranosyl (1→6)-β-D-glucopyranosyl or α-L-rhamnopyranosyl (1→6)-β-D-glucopyranosyl group and $R^3$ is hydrogen atom or hydroxy group; except the case where $R_1$ and $R_3$ are hydrogen atom and $R_2$ is β-D-glucopyranosyl group;

(f) when $R^1$ is β-D-xylopyranosyl (1→2)-β-D-glucopyranosyl group, $R^2$ is β-D-xylopyranosyl (1→6)-β-D-glucopyranosyl or α-L-rhamnopyranosyl (1→6)-β-D-glucopyranosyl group and $R^3$ is hydrogen atom.

The invention includes non-toxic salts of the compounds (II).

Specific examples of the compounds to be included in the formula (I) are as follows:

20S-Protopanaxadiol-3-O-{[β-D-glucopyranosyl (1→2)-α-L-rhamnopyranosyl (1→6)]-β-D-glucopyranoside}-20-O-[β-D-glucopyranosyl (1→6)-β-D-glucopyranoside]-designated as "gynosaponin A" hereinafter.

20S-Protopanaxadiol-3-O-{[β-D-glucopyranosyl (1→2)-α-L-rhamnopyranosyl (1→6)]-β-D-glucopyranoside}-20-O-[α-L-rhamnopyranosyl (1→6)-β-D-glucopyranoside] . . . "gynosaponin B".

20S-Protopanaxadiol-3-O-{[β-D-glucopyranosyl (1→2)-α-L-rhamnopyranosyl (1→6)]-β-D-glucopyranoside}-20-O-β-D-glucopyranoside . . . "gynosaponin F".

20S-Protopanaxadiol-3-O-[β-D-glucopyranosyl (1→2)-β-D-glucopyranoside]-20-O-[α-L-rhamnopyranosyl (1→6)-β-D-glucopyranoside] . . . "gynosaponin E".

20S-Protopanaxadiol-3,20-bis-O-[α-L-rhamnopyranosyl (1→6)-β-D-glucopyranoside] . . . "gynosaponin G".

20S-Protopanaxadiol-3-O-[α-L-rhamnopyranosyl (1→6)-β-D-glucopyranoside]-20-O-β-D-glucopyranoside . . . "gynosaponin K".

20S-Protopanaxadiol-3-O-β-D-glucopyranoside-20-O-[β-D-xylopyranosyl (1→6)-β-D-glucopyranoside] . . . "gynosaponin I".

20S-Protopanaxadiol-3-O-β-D-glucopyranoside-20-O-[α-L-rhamnopyranosyl (1→6)-β-D-glucopyranoside] . . . "gynosaponin J".

20S-Protopanaxadiol-20-O-[β-D-xylopyranosyl (1→6)-β-D-glucopyranoside] . . . "gynosaponin M".

20S-Protopanaxadiol-20-O-[α-L-rhamnopyranosyl (1→6)-β-D-glucopyranoside] . . . "gynosaponin N".

20S,26-Hydroxyprotopanaxadiol-3-O-{[β-D-glucopyranosyl (1→2)-α-L-rhamnopyranosyl (1→6)]-β-D-glucopyranoside}-20-O-[α-L-rhamnopyranosyl (1→6)-β-D-glucopyranoside] . . . "gynosaponin O".

20S-Protopanaxadiol-3-O-[α-L-rhamnopyranosyl (1→6)-β-D-glucopyranoside]-20-O-[β-D-glucopyranosyl (1→6)-β-D-glucopyranoside] . . . "progynosapogenin $A_2$".

20S-Protopanaxadiol-3-O-{[β-D-glucopyranosyl (1→2)-α-L-rhamnopyranosyl (1→6)]-β-D-glucopyranoside} . . . "progynosapogenin A-AH".

20S,26-Hydroxyprotopanaxadiol-20-O-β-D-glucopyranoside . . . "progynosapogenin $O_1$".

20S,26-Hydroxyprotopanaxadiol-3-O-[β-D-glucopyranosyl (1→2)-β-D-glucopyranoside]-20-O-[α-L-rhamnopyranosyl (1→6)-β-D-glucopyranoside] . . . "gynosaponin P".

20S-Protopanaxadiol-3-O-[β-D-xylopyranosyl (1→2)-β-D-glucopyranoside]-20-O-[β-D-xylopyranosyl (1→6)-β-D-glucopyranoside] . . . "gynosaponin Q".

20S-Protopanaxadiol-3-O-[β-D-xylopyranosyl (1→2)-β-D-glucopyranoside]-20-O-[α-L-rhamnopyranosyl (1→6)-β-D-glucopyranoside] . . . "gynosaponin R".

20S-Protopanaxadiol-3-O-β-D-glucopyranoside-20-O-[β-D-glucopyranosyl (1→6)-β-D-glucopyranoside] ... "gynosaponin S".

20S,26-Hydroxyprotopanaxadiol-3-O-{[β-D-glucopyranosyl (1→2)-α-L-rhamnopyranosyl (1→6)]-β-D-glucopyranoside}-20-O-[β-D-glucopyranosyl (1→6)-β-D-glucopyranoside] ... "gynosaponin T".

20S,26-Hydroxyprotopanaxadiol-20-O-[β-D-xylopyranosyl (1→6)-β-D-glucopyranoside] ... "gynosaponin U".

Among the gynosaponins of the formula (I), gynosaponins A, B, E, F, G, I, J, K, M, N, O, P, Q, R, S, T and U are components of *Gynostemma pentaphyllum* and may be isolated from said plant or botanical similar plants thereto by the following method.

The botanical similar plants to *Gynostemma pentaphyllum* include Gynostemma burumacicum King ex Chakravarty, Gynostemma laxum Gogn., Gynostemma integrifoliola Cogn. and the like, all of which belong to Cucurbitaceae.

(ISOLATION OF GYNOSAPONINS)

Said plant is extracted with water or an aqueous lower aliphatic alcohol, the extract is treated with a non-ionic absorbing resin, the adsorbed substance is eluted with a lower aliphatic alcohol, the eluate is treated with an alumina and the adsorbed substance is eluted with a lower aliphatic alcohol or a water containing lower aliphatic alcohol, to obtain crude saponins. Then a solution of crude saponins is treated with a styrene adsorption resin and/or a silica gel.

More detailedly, the procedures are as follows.

Firstly, the plant is extracted with water or a water containing lower aliphatic alcohol. Examples of the water containing lower aliphatic alcohol are methanol or ethanol which contains 50 v/v% or less of water. The extraction is preferred to conduct under warming or heating. Further, the whole parts of the plant may be used, which may be finely cut or degreased by a conventional method before subjecting to the extraction. When a water containing lower aliphatic alcohol is used as an extraction solvent, it is preferred to concentrate the extract solution to remove the alcohol, add an appropriate quantity of water to the concentrate and to treat the resulting solution with a nonionic adsorption resin.

The nonionic adsorption resins are preferred to be high-porous styrene-vinylbenzene copolymers, e.g., Amberlite XAD-2 (Rohm & Haas Co., U.S.A.). It is convenient to pass the extract through a column packed with the adsorption resin, thereby the saponins being adsorbed on it.

Next, the saponins adsorbed are eluted with a lower aliphatic alcohol, preferably methanol or ethanol. Before this elution, the column is preferably washed with water or a lower aliphatic alcohol containing about 20% water.

The alcoholic eluate is treated with an alumina. It is also convenient to use a column packed with the alumina. Before the treatment with the alumina, the alcoholic eluate may be suitably concentrated. The adsorbed saponins are eluted with a lower aliphatic alcohol, or a water containing lower aliphatic alcohol, e.g., about 50% aqueous alcohol. Then the eluate is concentrated to obtain crude saponins.

The resulting crude saponins are substantially free from other components of the plant and contain gynosaponins A, B, E, F, G, I, J, K, M, N, O, P, Q, R, S, T and U. Each of these gynosaponins may be separated and purified by e.g., the following method.

(SEPARATION OF EACH OF GYNOSAPONINS)

The individual gynosaponin may be obtained by adsorbing the above crude saponins on a styrene adsorption resin and/or a silica gel and eluting therefrom. This treatment is usually repeated on any of the adsorbents. The repetition in the order of styrene adsorption resin-silica gel, however, is effective. The use of high pressure liquid chromatographic apparatus achieves quick and high separation.

An example of the styrene adsorption resins is Servachrom XAD-2 (Serva Co.,). Also, the silica gels may be ones which are usually used in column chromatography or liquid chromatography.

An appropriate example of the above procedures is further detailedly explained as follows.

The above crude saponins which are dissolved in water are adsorbed on the styrene adsorption resin, which is subjected to gradient elution using 20–99% methanol. The eluted fractions of 30–40% methanol and 45–99% methanol are concentrated, respectively.

The concentrate from the eluted fractions of 30–40% methanol is adsorbed on a silica gel and eluted with chloroform/lower aliphatic alcohol/water, preferably a lower layer of chloroform/methanol/water of 65:35:10. The eluate is separated to Fraction I and Fraction II, monitoring by thin layer chromatography. Fractions I and II are treated with a silica gel in a conventional way (the eluting solvent:n-butanol/ethyl acetate/water of 14:3:3) and then with a modified silica in a reverse way (the eluting solvent of 35–39% ethanol). The use of high pressure liquid chromatographic apparatus is efficient. Gynosaponin P is obtained from Fraction I, and gynosaponin O and T from Fraction II.

On the other hand, the concentrate of the fractions of 40–99% methanol is, in the same way as above, adsorbed on a silica gel and eluted preferably with a lower layer of chloroform/methanol/water of 65:35:10 to yield Fractions I–VI. By the treatment of these Fractions in a way similar to the above, gynosaponin M, N and U are obtained from Fraction I; gynosaponin I, J and K from Fraction II; gynosaponin G, Q, R and S from Fraction III; gynosaponin E and F from Fraction IV; gynosaponin B from Fraction V, and gynosaponin A from Fraction VI, respectively. Simultaneously, gynosaponin C, D, H and L which are found to have known structures and are hereinafter explained, can be isolated.

Thus, according to one aspect of the invention, it provides a method for isolating gynosaponins from Gynostemma pentaphyllum or botanical similar plant thereto belonging to Cucurbitaceae, and a method for separating individual gynosaponin [including the compound of the formula (I)] from said gynosaponins.

A further aspect of the invention is to provide a method for preparing a group of saponins by an enzymatic or acid hydrolysis of the compound of the formula (I), or the formula (II) as described hereinafter.

(ENZYMATIC HYDROLYSIS)

When the compound of the above mentioned formula (I) is subjected to an enzymatic hydrolysis, it may produce the compound of the formula (I) wherein at least one carbohydrate moiety is removed from its substituents at the 3rd and/or 20th positions.

It is conducted by contacting the compound (I) with an enzyme. The enzyme used is selected from enzymes which possess an ability of being capable to split off O-glycosidic bond. Preferred examples of the enzymes are hesperidinase, maltase, cellulase, takadiastase and the like. Other examples are naringinase, pectinase, amylase and emulsin. These enzymes may be in crude or purified form.

The use quantity of the enzyme is different in its sort, but for example that of cellulase is about 600–1,000 units per one gram of the compound (I).

The enzymatic reaction is preferred to conduct under an acidic condition, e.g., in a buffer solution of a pH of about 4. The acidity may be varied upon the sorts of the enzymes.

The reaction temperatures may be at room temperature or elevated temperature, generally at 30°–40° C., although it is non-limitative. The reaction period varies on the sort or purification degree of the enzyme, the reaction temperature, the degree of hydrolysis to be aimed, generally for a few hours or one week.

When the compound (I) is hydrolyzed under the above conditions, at least one carbohydrate moiety may be removed from the substituents at the 3rd and 20th position. For example, the 3rd substituents may be converted as: glucopyranosyl group to hydrogen atom, glucopyranosyl-glucopyranosyl group or rhamnopyranosyl group to glucopyranosyl group or hydrogen atom, glucopyranosyl-rhamnopyranosyl-glucopyranosyl group to rhamnopyranosyl-glucopyranosyl group, glucopyranosyl group or hydrogen atom. The case of the 20th substituents is the same as above.

According to the invention, a selective removal for one carbohydrate moiety may be achieved by selecting a suitable condition. The removal for two or more carbohydrate moieties is possible. However, it is desired to stop the hydrolysis so as to leave one or more carbohydrate moieties.

Furthermore, when plural hydrolysates are produced, they may be separated into individual compound by using a technique similar to those of isolation and purification of the extract of the above mentioned plant. Also, the compounds of the formula (I) may be used in the form of mixture for the above hydrolysis.

Under the above mentioned hydrolysis, for example, gynosaponin A may be converted into gynosaponin F, progynosaponin A₂, gynosaponin K, ginsenoside F₂ (a known component isolated from Panax ginseng) and "Compound K" (a prosapogenin of a saponin of Panax ginseng). The former three compounds belong to the formula (I).

(ACID HYDROLYSIS)

When the compound (I) wherein R³ is hydrogen atom is subjected to an acid hydrolysis, it may produce the compound wherein one or more carbohydrate moieties are removed from the substituents at the 20th position.

It is conducted to react the compound (I) with a weak acid. Preferred examples of the weak acids are water-soluble lower aliphatic carboxylic acids such as acetic acid. The most preferred example is 40–60% acetic acid aqueous solution.

The reaction may be conducted at room temperature or elevated temperature (e.g., at 70°–80° C.). The use quantity of the acid is generally 100–1,000 mols to one mol of the saponins, preferably 270–630 mols.

Under such condition, the 20th substituents may be selectively hydrolyzed, while the 3rd substituents are unchangeable. More concretely, glucopyranosyl group, glucopyranosyl-glucopyranosyl group, xylopyranosyl-glucopyranosyl group or rhamnopyranosyl group may be converted into hydrogen atom.

The separation of the hydrolysates may be conducted as explained in the enzymatic hydrolysis. And the compounds of the formula (I) wherein R³ is hydrogen atom may be used in the form of mixture for the hydrolysis.

Thus, for example, gynosaponin A or B is converted into progynosapogenin A-AH [R² is hydrogen and R¹ is β-D-glucopyranosyl (1→2)-α-L-rhamnopyranosyl (1→6)-β-D-glucopyranosyl group].

A still further aspect of the invention is to provide a method for isolating a compound of the below mentioned formula (II) from Gynostemma pentaphyllum or botanical similar plant thereto and a method for removing one or more carbohydrate moieties at the 3rd and/or 20th position of the compound of the formula (II).

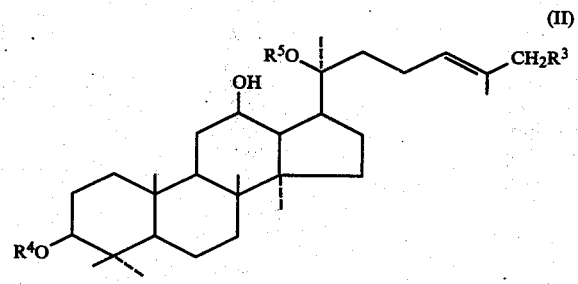

(II)

In the formula (II), R⁴ is β-D-glucopyranosyl (1→2)-β-D-glucopyranosyl group and R⁵ is β-D-glucopyranosyl (1→6)-β-D-glucopyranosyl group, β-D-xylopyranosyl (1→6)-β-D-glucopyranosyl group or β-D-glucopyranosyl group; or R⁴ is β-D-glucopyranosyl group and R⁵ is β-D-glucopyranosyl group.

Also, the invention includes non-toxic salts of the compounds of the formula (II).

Specific names of the compounds of the formula (II) are as follows.

20S-Protopanaxadiol-3-O-[β-D-glucopyranosyl (1→2)-β-D-glucopyranoside]-20-O-[β-D-glucopyranosyl (1→6)-β-D-glucopyranoside] . . . designated as "gynosaponin C".

20S-Protopanaxadiol-3-O-[β-D-glucopyranosyl (1→2)-β-D-glucopyranoside]-20-O-[β-D-xylopyranosyl (1→6)-β-D-glucopyranoside] . . . "gynosaponin D".

20S-Protopanaxadiol-3-O-[β-D-glucopyranosyl (1→2)-β-D-glucopyranoside]-20-O-β-D-glucopyranoside . . . "gynosaponin H".

20S-Protopanaxadiol-3,20-di(O-β-D-glucopyranoside) . . . "gynosaponin L".

The above mentioned gynosaponins of the formula (II) can be obtained when the compounds (I) are isolated at the above mentioned procedure.

The gynosaponins of the formula (II) may be converted into other saponins by hydrolyzing carbohydrate chain thereof.

For example, an enzymatic hydrolysis of gynosaponin C gives gynosaponin H, gynosaponin L and progynosapogenin A₁ [the compound of the formula (I) wherein R¹ is hydrogen, R² is β-D-glucopyranosyl and R³ is hydrogen; mp 154°–156° C.). Also, an enzymatic hydrolysis of gynosaponin D gives gynosaponins H, I and M and progynosapogenin A₁.

The details of the above enzymatic hydrolysis are the same as those given for the compound (I).

Also, an acid hydrolysis of the compounds (II) under the same condition as in the compound (I) will achieve the selective removal for the 20th substituent, while the 3rd substituent is unchangeable. That is, glucopyranosyl group, glucopyranosyl-glucopyranosyl or xylopyranosyl-glucopyranosyl group as the 20th substituent can be hydrolyzed to hydrogen atom.

Of course, when the hydrolysis gives a mixture of the hydrolysates, an isolation technique similar to that of the compounds of the formula (I) or (II) is applicable to the hydrolysates.

The non-toxic salts of the compounds of the formula (I) or (II) include pharmaceutically acceptable salts such as the alkali metal (e.g., Na, K) salts and alkali earth metal (e.g., Ca, Mg) salts.

According to another aspect of this invention, there is provided a pharmaceutical composition containing as an effective ingredient the entire saponin isolated from Gynostemma pentaphyllum, or the compound of the aforesaid formula (I).

The saponins obtained from Gynostemma pentaphyllum act on the cells of animals, including man, and are useful as an antiulcerous agent, an agent for preventing the side effects of glucocorticoids, a cell activator, an antitumorous agent and an agent for promoting lipid metabolism. They also act on the central nerves, and are useful as an agent for improving general malaise, a sedative and a hypnotic.

It is generally preferable from an economical standpoint to use these saponins in the form of a mixture, rather than in the form of the individual saponins. The term "saponin component" as herein used refers to a mixture composed essentially solely of saponins.

The saponin component has an extremely low degree of toxicity. It showed a $LD_{50}$ of 755 mg/kg when intraperitoneally injected into mice. It produced virtually no side effect when administered to man.

The composition of this invention may be used in the form of either an internal preparation for oral administration, or an injection or external preparation for parenteral administration. It comprises the saponin component, and a solid or liquid excipient or a carrier.

It is most preferable to use the composition of this invention in the form of an internal preparation. Such an internal preparation may usually be obtained in the form of a powder, a tablet, an emulsion, a capsule, a tea, a granule, or a liquid, including a fluid extract and a syrup.

Specific examples of the excipients which can be used for internal preparations include lactose, starch, dextrin, calcium phosphate, calcium carbonate, synthetic and natural aluminum silicate, magnesium oxide, desiccated aluminum hydroxide, magnesium stearate, sodium bicarbonate and dry yeast for preparing a powder or powdered drug for internal administration. Examples of the excipient for preparing a powder for external use may include zinc oxide, talc, starch, kaolin, boric acid powder, zinc stearate, magnesium stearate, precipitated calcium carbonate, bismuth digallate, and potassium aluminum sulfate powder. For a liquid preparation, it is possible to use such an excipient as water, glycerin, propylene glycol, simple syrup, ethanol, fatty oil, ethylene glycol, polyethylene glycol, and sorbitol.

Sterilized distilled water may, for example, be used as a liquid excipient for preparing an injection.

Examples of the dosage forms which external preparations may take include a suppository, an ointment, a solution, a powder for external use, a fomentation, a spray, a clyster, and an emulsion. The solid or liquid excipient for use in this invention may be selected from among those known in the art. For example, an excipient for an ointment may comprise a hydrophobic or hydrophilic base, including an emulsion base, a water-soluble base and a suspension base, prepared by combining fat, fatty oil, lanolin, vaseline, yellow wax, vegetable wax, paraffin, fluid paraffin, a resin, a higher alcohol, plastics, glycols, water, a surface active agent, or the like.

Any of other usual additives known in the arts may be used in the compositions of the invention.

While the aforesaid preparations can be manufactured by any appropriate method known in the art, it is desirable to ensure that each individual dosage form contain a single dose of the saponin component according to this invention. These preparations are subject to selective use in the most suitable and convenient form for the purpose intended.

The dosage of the saponin component defining an essential effective constituent of the pharmaceutical composition according to this invention depends to some extent on the purpose for which it is used, and will hereinafter be described for each of various applications.

The saponin component of this invention is effective as a sedative or hypnotic, an agent for improving general malaise and a cell activator for preventing ageing, removing fatigue, or the like. These effects of the saponin component can be obtained if an adult uses it in the amount of 20 to 500 mg, preferably 50 to 300 mg, per day, and takes it in two or three installments every day. Either oral or parenteral administration may be satisfactory. The oral administration may be realized in the form of any of the aforesaid internal preparations, while the parenteral administration may take the form of an injection, or a suppository or hydrophilic ointment for absorption through the rectum or mucous membrane. It is desirable that each administration should have a concentration of the saponin component in the range of 5 to 50 mg/ml in the case of an injection, and 0.1 to 10% by weight in the case of a suppository or ointment.

The saponin component of this invention is also very useful as a medicine for curing an ulcer in man. The dosage of the saponin component required for curing an ulcer depends on the condition of the disease, but in the event it is internally used for an adult, it usually manifests its efficacy if administered in two or three doses in the amount of 50 to 1,000 mg, preferably 100 to 250 mg, per day. It is effectively applicable for curing a gastric or duodenal ulcer, or the like.

The saponin component of this invention is also useful as an antitumorous drug for human being. The suitable dosage of the saponin component as an antitumorous drug depends on the condition of the disease, but generally, it manifests its efficacy if it is administered in the amount of 50 to 1,000 mg, preferably 100 to 300 mg, per day in two or three doses in case the patient is an adult. It may be administered in any form, whether in the form of an internal preparation, injection or external preparation, depending on the condition of the disease.

Glucocorticoids (e.g., cortisone), which belong to adrenocortical hormones, are widely used as medicines for protecting a living body from stress, and participating in the conversion of proteins to carbohydrate, lipid metabolism, or the like. The continuous use of these medicines is, however, likely to cause serious trouble to the internal organs, such as atrophy of the adrenal cortex, while at the same time, they produce various side effects known under the name of Cushing's syndrome, including abnormal deposition of fat or edema in the face, neck, body or the like, such as a moon face and a buffalo's neck, abnormal increase of appetite, increase in body weight, pigmentation in the skin and nails, cornification of the skin, hyperglycemia, hypertension, reduction in the muscle force, hypokalemia, and worsening of any existing ulcer.

When used in combination with a glucocorticoid, the saponin component of this invention can cure and prevent any serious trouble caused by the glucocorticoid in the internal organs.

Thus, the saponin component of this invention is distinctly effective against the adrenal atrophy caused by the use of glucocorticoids and the accompanying reduction in the amount of plasma cortisol. Therefore, it is useful for curing troubles resulting from the adrenal atrophy, and any side effect associated therewith.

The suitable dosage of the saponin component for curing any disease due to the side effects of glucocorticoids depends on the condition of the disease, but generally, it may be administered in three or four doses in the amount of 5 to 500 mg, preferably 10 to 250 mg, per day if it is internally used for an adult patient.

The dosage of a glucocorticoid depends on the type of the compound to be used, the condition of the disease, or the like. For example, cortisone, which is a typical glucocorticoid, is usually used in the amount of 5 to 30 mg per day, though it may sometimes be used in the amount of as much as 200 to 400 mg per day for the initial treatment of a patient who suffers from an acute disease.

In the event a glucocorticoid and the saponin component are used together, it is preferable to incorporate them into a single dosage form. For this purpose, it is possible to adopt any dosage form known in the art for glucocorticoids. Both a dosage form for oral administration and one for parenteral use are satisfactory.

A preparation for oral use should preferably contain 5 to 100 mg of the saponin component and 0.5 to 10 mg of a glucocorticoid per gram or tablet. An external preparation for parenteral use should preferably contain 0.1 to 10% (W/V) of the saponin component and 0.05 to 1% (W/V) of a glucocorticoid.

An injection for parenteral use should preferably contain 5 to 50 mg of the saponin component and 1 to 20 mg of a glucocorticoid per milliliter.

In the event it is desired to administer the saponin component alone, it is possible to employ any dosage form, whether it may be an internal preparation, an injection or an external preparation.

The isolation of Gynosaponins is explained by the following examples.

EXAMPLE 1

Dried whole parts of Gynostemma pentaphyllum (2 Kg) were twice extracted with 30 l of water under heating. The combined extracts were passed through a column packed with 4 l of Amberlite XAD-2, a non-ionic adsorption resin. After washing with 10 l of water and with 6 l of 20% methanol, the adsorbed substances were eluated with 5 l of methanol. The eluate was evaporated to dryness under reduced pressure to yield 37 g of a yellowish brown powder.

A solution of this powder in 1 l of methanol was passed through an alumina (300 g) column. The adsorbed substances were eluated with about 20 l of 50% methanol. The eluate was concentrated under reduced pressure to yield 25 g of crude gynosaponins as a pale-yellow powder.

A solution of 20 g of crude gynosaponins in 1 l of water was passed through a column packed with 600 ml of Servachrom XAD-2, a styrene adsorption resin. The adsorbed substances were eluted with 20-99% methanol, increasing stepwise the methanol content from 20% to 99%. The combined eluates by 45-99% methanol were evaporated to dryness under reduced pressure to yield 16 g of a pale-yellow powder.

The powder was subjected to a silica gel (300 g) column chromatography followed by fractional elution with each of 100 ml of a lower layer of a mixture of chloroform/methanol/water of 65:35:10, to obtain Fractions 1-6, while the eluates were monitored by a thin layer chromatography (TLC).

Each of Fractions 1-6 was evaporated to dryness. Each concentrates from Fractions 1-3 was subjected to a silica gel (100 g) column chromatography followed by fractional elution with a lower layer of a mixture of chloroform/methanol/ethyl acetate/water of 2:2:4:1. This procedure was repeated twice. Gynosaponin M (60 mg) and 160 mg of gynosaponin N were obtained from Fraction 1 (1.1 g); 60 mg of gynosaponin I, 120 mg of gynosaponin J and 110 mg of gynosaponin K from Fraction 2 (1.0 g); and 450 mg of gynosaponin G from Fraction 3 (1.0 g).

Also, each concentrates from Fractions 4 and 5 was subjected to a silica gel (200 g) column chromatography using an upper layer of a mixture of n-butanol/ethyl acetate/water of 4:1:2, three times. Gynosaponin D (350 mg), 1500 mg of gynosaponin E and 80 mg of gynosaponin F were obtained from Fraction 4 (3.4 g); and 220 mg of gynosaponin B and 240 mg of gynosaponin C from Fraction 5 (2.5 g).

Further, 510 mg of gynosaponin A were obtained by twice column chromatography (100 g of silica gel, a lower layer of chloroform/methanol/water of 65:35:10).

The physical properties of these gynosaponins are shown in Tables 1 and 2.

EXAMPLE 2

Dried whole parts of Gynostemma pentaphyllum (2 Kg) were twice extracted with 30 l of water under heating. The combined extracts were passed through a column packed with 4 l of Amberlite XAD-2, a non-ionic adsorption resin (average particle diameter: 0.45-0.60 mm, Rohm & Haas Co., in U.S.A.). After washing with 10 l of water and with 6 l of 20% methanol, the adsorbed substances were eluted with 5 l of 99% methanol. The eluate was evaporated to dryness under reduced pressure to yield 37 g of a yellowish brown powder. A solution of this powder in 1 l of 99% methanol was passed through a column packed with alumina (300 g) (neutral, 70-290 mesh, Woelm Co.). The adsorbed substances were eluted with about 20 l of 50% methanol. The eluate was evaporated to dryness under reduced pressure to yield 25 g of a fraction of crude gynosaponins as a pale-yellow powder.

A solution of 20 g of the fraction of crude gynosaponins in 1 l of water was passed through a column packed with 600 ml of Servachrom XAD-2, adsorption resin, (average particle diameter: 100-200 μm, from Serva Co.). The adsorbed substances were eluted with 20–99% methanol, increasing the methanol content by the step of 5% from 20% to 99%. The combined eluates with 30–40% methanol (40 l) were evaporated to dryness under reduced pressure to yield 2 g of a pale-yellow powder and the combined eluates with 45–99% methanol were evaporated to dryness under reduced pressure to yield 16 g of a pale-yellow powder.

A solution of 2 g of the fraction from the eluate with 30–40% methanol in minimum quantity of 99% methanol of was mixed sufficiently with 4 g of silica gel and the mixture was evaporated to dryness under reduced pressure. The residue was placed on a column packed with 200 g of silica gel (230–400 mesh ASTM, Merck & Co.) in dry state and then eluted with a lower layer of a mixture of chloroform/methanol/water of 65:35:10, to obtain Fractions I and II, while the eluates were monitored by TLC (adsorbent: silica gel, developing solvent: a lower layer of chloroform/methanol/water of 65:35:10, detecting agent: 30% sulfuric acid). Each of Fractions I and II was evaporated to dryness under reduced pressure. About 0.7 g of Fraction I and about 0.9 g of Fraction II were separately subjected to a high pressure liquid chromatography using the chromatograph (Waters Co. ALC/GPC type) with a column below mentioned, while the eluates were monitored by TLC to obtain 120 mg of gynosaponin P from Fraction I, and 150 mg of gynosaponin O and 60 mg of gynosaponin T from fraction II.

Porasil A columns (37–75μ, from Japan Waters Ltd., 7 mm×61 cm×4 pieces) and Nucleosil 30 $C_{18}$ columns (30±4μ, M-NAGEL in West Germany 7 mm×61 cm×2 pieces) were used as columns, and a mixture of n-butanol/ethyl acetate/water of 14:3:3 and 35–39% ethanol were used as mobile phases, respectively.

A solution of 16 g of the fraction from the eluate with 45–99% methanol in minimum quantity of 99% methanol was sufficiently mixed with 30 g of silica gel and the mixture was evaporated to dryness under reduced pressure. The residue was placed on a column packed with 300 g of silica gel in dry state and then eluted with a lower layer of a mixture of chloroform/methanol/water of 65:35:10 to obtain Fractions 1–6, while the eluates were monitored by TLC (adsorbent: silica gel, solvent: a lower layer of chloroform/methanol/water of 65:35:10, detecting agent: 30% sulfuric acid). Each of Fractions 1–6 was evaporated to dryness under reduced pressure.

Each solution of about 1.1 g of Fraction 1, about 1.1 g of Fraction 2 and about 1.0 g of Fraction 3 in minimum quantity of 99% methanol was sufficiently mixed with 3 g of silica gel and each of mixtures was evaporated to dryness under reduced pressure. Each of residues was placed on a column packed with 100 g of silica gel of dry state and then eluted with a lower layer of a mixture of chloroform/methanol/ethyl acetate/water of 2:2:4:1. Further this procedure was twice repeated respectively to obtain 350 mg of gynosaponin L, 60 mg of gynosaponin M and 160 mg of gynosaponin N from Fraction 1; 150 mg of gynosaponin H, 60 mg of gynosaponin I, 120 mg of gynosaponin J and 110 mg of gynosaponin K from Fraction 2; and 450 mg of gynosaponin G from Fraction 3.

Each of residues after the above treatment of Fractions 1 and 3 was subjected to a high pressure liquid chromatography using the chromatograph with a column below mentioned to obtain 30 mg of gynosaponin U from the residue of Fraction 1; and 25 mg of gynosaponin Q, 40 mg of gynosaponin R and 30 mg of gynosaponin S from the residue of Fraction 3.

Porasil A columns (7 mm×61 cm×4 pieces; mobile phase: n-butanol/ethyl acetate/water of 14:3:3) and Nucleosil 30 $C_{18}$ columns (7 mm×61 cm×2 pieces; mobile phase: 40–45% ethanol) were used.

Each solution of about 3.4 g of Fraction 4 and about 2.5 g of Fraction 5 in 99% methanol of minimum volume was sufficiently mixed with 6 g of silica gel and each of mixtures was evaporated to dryness under reduced pressure. Each of residues was placed on a column packed with 200 g of silica gel of dry state and then eluted with an upper layer of a mixture of n-butanol/ethyl acetate/water of 4:1:5. Further, this procedure was twice repeated respectively to obtain 350 mg of gynosaponin D, 1500 mg of gynosaponin E and 80 mg of gynosaponin F from Fraction 4; and 220 mg of gynosaponin B and 240 mg of gynosaponin C from Fraction 5, respectively.

Further, about 0.9 g of Fraction 6 was eluted by a lower layer of a mixture of chloroform/methanol/water of 65:35:10 in accordance with above-mentioned procedure to obtain 510 mg of gynosaponin A.

The physical properties of gynosaponins are shown in Tables 1 and 2.

Gynosaponins C, D, H and L were identical with ginsenoside —$Rb_1$, —$Rb_3$, —Rd and —$F_2$ of ginseng saponins respectively by directly comparing physical properties and NMR data.

EXAMPLE 3

To a solution of 250 mg of gynosaponin A in 50 ml of an aqueous solution of 0.005 M sodium dihydrogenphosphate (pH 4.0) was added 500 mg of crude hesperidinase (TANABE SEIYAKU CO., LTD.) and the mixture was stirred for 6 hours at 37°–38° C. The reaction mixture was passed through a column packed with 50 ml of Servachrom XAD-2, styrene adsorption resin (from Serva Co.) After washing with 1 l of water and with 2 l of 20% methanol, the adsorbed substances were eluted with 300 ml of methanol. The eluate was concentrated under reduced pressure and the concentrate was subjected to a silica gel column chromatography and eluted with a lower layer of a mixture of chloroform/methanol/water of 65:35:10 to obtain 20 mg of gynosaponin F, 15 mg of gynosaponin K and 35 mg of progynosapogenin $A_2$. Gynosaponins F and K were identical with the standard samples obtained at Example 1 by comparing IR and NMR data.

The physical properties of progynosapogenin $A_2$ are shown in Tables 1 and 2 described hereinafter.

EXAMPLE 4

A solution of 150 mg of gynosaponin A in 10 ml of 50% acetic acid was stirred for 6 hours at 70° C. The reaction mixture was passed through a column packed with 50 ml of Servachrom XAD-2, styrene adsorption resin to obtain about 100 mg of the fraction of prosapogenin. This fraction was subjected to a silica gel column chromatography and then eluted with a lower layer of a mixture of chloroform/methanol/ethyl acetate/water of 2:2:4:1 to obtain 35 mg of progynosapogenin A-AH.

The physical properties of this product are shown in Tables 1 and 2 described hereafter.

EXAMPLE 5

Gynosaponin A (400 mg) was dissolved in 50 ml of an aqueous solution of 0.005 M sodium dihydrogenphosphate (pH 4.0). To this solution was added 300 mg of cellulase (from Sigma Co.) and the mixture was stirred for 24 hours at 37°–38° C. The reaction mixture was treated in the same manner as described in Example 2 to obtain 110 mg of gynosaponin K, 35 mg of gynosaponin L and 20 mg of progynosapogenin $A_1$. Gynosaponins K and L were identical with the standard samples obtained in Example 1 by comparing IR and NMR data. Also progynosapogenin $A_1$ was the same as the compound K which can be obtained by an enzymatic decomposition of the ginseng saponin.

EXAMPLE 6

A mixture (1.4 g) of gynosaponins B and C was dissolved in 200 ml of an aqueous solution of 0.005 M sodium dihydrogen phosphate (pH 4.0). To this solution was added 600 mg of cellulase (from Sigma Co.) and the mixture was stirred for 7 hours at 37°–38° C. The reaction mixture was passed through a column of 80 ml of Servachrom XAD-2 to obtain about 1.1 g of hydrolysate. This product was subjected to a silica gel column chromatography and then eluted with a lower layer of chloroform/methanol/ethyl acetate/water of 2:2:4:1 to obtain 17 mg of progynosapogenin $A_1$, 190 mg of gynosaponin L, 140 mg of gynosaponin K; and 550 mg of a mixture of gynosaponins F, G and H. This mixture was again subjected to a silica gel column chromatography and then eluted with a lower layer of chloroform/methanol/water of 65:35:10 to obtain 50 mg of gynosaponin F, 150 mg of gynosaponin G and 210 mg of gynosaponin H. These gynosaponins were identical with standard samples by comparing IR and NMR data.

EXAMPLE 7

A solution of 300 mg of a mixture of gynosaponins B and C in 10 ml of 50% acetic acid was stirred for 6 hours at 70° C. The reaction mixture was passed through a column packed with 50 ml of Servachrom XAD-2 to obtain the fraction of prosapogenins, which was subjected to a silica gel column chromatography and then eluted with a lower layer of a mixture of chloroform/methanol/water of 65:35:10 to obtain 30 mg of progynosapogenin A-AH and 70 mg of progynosapogenin E-AH. This progynosapogenin A-AH was identical with the standard sample obtained in Example 4 by comparing IR and NMR data. Also the progynosapogenin E-AH was identical with ginsenoside-$Rg_3$ which is a hydrolysate of the ginseng saponin by 50% acetic acid.

EXAMPLE 8

A mixture (2 g) of gynosaponins D and E was dissolved in 0.005 M sodium dihydrogen phosphate (pH 4.0). To this solution was added 1 g of cellulase (Sigma Co.) and the mixture was stirred for 20 hours at 37°–38° C. The reaction mixture was treated with a column packed with 80 ml of Servachrom XAD-2 to obtain about 1.6 g of a hydrolysate. The product was subjected to a silica gel column chromatography and eluted with a lower layer of a mixture of chloroform/methanol/ethyl acetate/water of 2:2:4:1 to obtain 20 mg of gynosaponin H, 355 mg of gynosaponin I, 250 mg of gynosaponin J, 80 mg of gynosaponin M, 90 mg of gynosaponin N and further 70 mg of progynosapogenin $A_1$.

These saponins were identical with the standard samples by comparing IR and NMR data.

EXAMPLE 9

Gynosaponin E (5 mg) was dissolved in 1 ml of 0.005 M aqueous sodium dihydrogen phosphate (pH 4.0). To this solution was added 10 mg of cellulase and the mixture was stirred for 4 hours at 37°–38° C. It was confirmed by TLC that in the reaction mixture gynosaponins H, L and N, and progynosapogenin $A_1$ were formed.

EXAMPLE 10

A solution of 350 mg of gynosaponin E in 10 ml of 50% acetic acid was stirred for 6 hours at 70° C. The reaction mixture was treated in the same manner as in Example 4 to obtain about 210 mg of prosapogenin fraction. This fraction was dissolved in minimum quantity of 99% methanol and mixed well with 1 g of silica gel. The mixture was evaporated to dryness under reduced pressure. The residue was placed on a column packed with 50 g of silica gel in dry state and eluted with a lower layer of a mixture of chloroform/methanol/ethyl acetate/water of 2:2:4:1 to obtain 140 mg of propynosapogenin E-AH.

EXAMPLE 11

The crude gynosaponin obtained in Example 1 was treated with Servachrom XAD-2 and eluted with 30–40% methanol. The eluate was evaporated to dryness under reduced pressure to obtain 2 g of pale-yellow powder. This powder was subjected to a silica gel (200 g) column chromatography and eluted with a lower layer of chloroform/methanol/water of 65:35:10. In addition, this procedure was twice repeated to obtain 150 mg of gynosaponin O. The physical properties of this product are shown in Tables 1 and 2 described hereafter.

EXAMPLE 12

To a solution of 150 mg of gynosaponin O in 30 ml of 0.005 M sodium dihydrogen phosphate was added 150 mg of cellulose (Sigma Co.) and the mixture was stirred for 24 hours at 37°–38° C. The reaction mixture was treated in the same manner as in Example 3 to obtain 20 mg of progynosapogenin $O_1$. The physical properties of this product are shown in Tables 1 to 2.

EXAMPLE 13

To a solution of 5 mg of gynosaponin C in 1 ml of 0.005 M sodium dihydrogen phosphate (pH 4.0) was added 10 mg of cellulase and the mixture was stirred for 6 hours at 37°–38° C. It was confirmed that in the reaction mixture gynosaponins H and L and progynosapogenin $A_1$ were formed, by TLC (adsorbent: silica gel, solvent: a lower layer of chloroform/methanol/water of 65:35:10 or chloroform/methanol/ethyl acetate/water of 2:2:4:1, detecting reagent: 30% sulfuric acid).

EXAMPLE 14

To a solution of 5 mg of gynosaponin D in 1 ml of 0.005 M sodium dihydrogen phosphate (pH 4.0) was added 10 mg of cellulase and the mixture stirred for 4 hours at 37°–38° C. It was confirmed by TLC that gynosaponins H, I, L and M and progynosapogenin $A_1$ were formed in the reaction mixture.

EXAMPLE 15

To a solution of 2 g of a mixture of gynosaponins D and E in 200 ml of 0.005 M sodium dihydrogen phosphate (pH 4.0) was added 1 g of cellulase and the mixture was stirred for 20 hours at 37°–38° C. The reaction mixture was treated by a column packed with 80 ml of Servachrom XAD-2 to obtain about 1.6 g of a hydrolysate. This product was dissolved in a minimum quantity of 99% methanol and mixed well with 3 g of silica gel and the mixture was evaporated to dryness under reduced pressure. The residue was placed on a column packed with 200 g of silica gel in dry state and eluted with a lower layer of chloroform/methanol/ethyl acetate/water of 2:2:4:1 to obtain 20 mg of gynosaponin H, 355 mg of gynosaponin I, 250 mg of gynosaponin J, 270 mg of gynosaponin L, 80 mg of gynosaponin M, 90 mg of gynosaponin N and 70 mg of progynosapogenin $A_1$.

These gynosaponins H, I, J, L, M and N and progynosapogenin $A_1$ were identical with the standard samples by TLC and PMR.

EXAMPLE 16

A solution of 30 mg of gynosaponin C in 2 ml of 50% acetic acid was stirred for 6 hours at 70° C. The formation of progynosapogenin E-AH was confirmed, by using TLC (adsorbent: silica gel, solvent: a lower layer of a mixture of chloroform/methanol/water of 65:35:10 or an upper layer of n-butanol/ethyl acetate/water of 4:1:5, detecting agent: 30% sulfuric acid).

EXAMPLE 17

A solution of 150 mg of gynosaponin D in 10 ml of 50% acetic acid was stirred for 6 hours at 70° C. The reaction mixture was passed through a column packed with 50 ml of Servachrom XAD-2. After washing with 1 l of water and with 2 l of 30% methanol, the adsorbed substance was eluted with 300 ml of 99% methanol. The eluate was evaporated to dryness under reduced pressure to obtain about 90 mg of the residue. A solution of the residue in a minimum quantity of 99% methanol was sufficiently mixed with 1 g of silica gel. The mixture was evaporated to dryness under reduced pressure. The residue was placed on a column packed with 50 g of silica gel of dry state and eluted with a lower layer of chloroform/methanol/water of 65:35:10 to obtain 30 mg of progynosapogenin E-AH.

This compound was identical with gensenoside-$Rg_3$ which is produced by the hydrolysis of a ginseng saponin with 50% acetic acid.

EXAMPLE 18

Dried whole parts of *Gynostemma pentaphyllum* (10 Kg) were chopped and extracted three times with three 100 ml portions of methanol under heating for 3 hours. The combined extract was concentrated up to 5 l. The concentrate was gradually poured into 50 l of ethyl ether with stirring and the resulting precipitate was filtered and dried until no smell of ether is recognized. The product was dissolved in 10 l of n-butnaol saturated with water, under heating on steam bath and stirring. The obtained solution was three times washed with 3 l of water saturated with n-butanol to remove saccharide or colorants as contamination. The water saturated n-butanol layer which was separated was evaporated to dryness under reduced pressure below 80° C. A solution of the residue in 3 l of methanol was poured into 60 l of ethyl ether with stirring. After standing for one day, a precipitate was filtered and was dried under reduced pressure below 60° C. to obtain 125 g of saponins (yield: 1.25%).

The obtained saponin has the following properties:

1. it is odorless, pale-yellow or brown powder, has bitter taste a little and is readily soluble in methanol, soluble in water and ethanol, and insoluble in benzene, chloroform, ether, hexane and petroeum ether.
2. its 1% aqueous solution is neutral.
3. when present KBr disc, it has a infra-red spectrum which has absorption maxima at 3370, 1650, 1070 and 1040 $cm^{-1}$.
4. it has a NMR spectrum in pyridine-$d_5$ which has peaks at 4.0 (broad), 1.6 (broad), 1.2 (broad) and 0.9 ppm (broad).
5. when shaked with water, it produces sustaining small foams.
6. it is positive in Liebermann's reaction and Salkowski reaction.
7. from the water-soluble part of its acid hydrolysate, glucose, rhamnose and xylose and obtained; and from the water-insoluble part of said hydrolysate, panaxadiol ($C_{30}H_{52}O_3$, mp:205° C.) and a small quantity of 26-hydroxyl panaxadiol are obtained.
8. when subjected to TLC below-mentioned, it shows saponin spots of red purple color.
   plate : Kieselguhr, 60 $F_{254}$ (Merck)
   developing solvent: lower layer of a mixture of chloroform/methanol/water of 65:35:10
   developing distance: 10 cm
   detection: after spraying 1% ceric sulfate −10% sulfuric acid, heating for 5 minutes at 105° C.

TABLE 1

| | mp(°C.) | Formula | Elementary Analysis Calcd. C % | Calcd. H % | Found C % | Found H % | Rotation $[\alpha]_D^{22°}$ | MeOH | $[M]_D$ | IR |
|---|---|---|---|---|---|---|---|---|---|---|
| Gynosaponin A | 201–203 | $C_{60}H_{102}O_{27} \cdot 3H_2O$ | 55.03 | 8.31 | 54.78 | 8.57 | −1.38° | (c=1.5) | −18.1° | 3375, 1640, 1160, 1075, 1045, 1015, 985 |
| Gynosaponin B | 196–198 | $C_{60}H_{102}O_{26} \cdot 3H_2O$ | 55.71 | 8.42 | 55.63 | 8.56 | −3.30° | (c=1.5) | −42.7° | 3375, 1635, 1160, 1070, 1045, 1015, 985 |
| Gynosaponin E | 199–201 | $C_{54}H_{92}O_{22} \cdot 3H_2O$ | 56.52 | 8.61 | 56.33 | 8.86 | +8.61° | (c=1.4) | +98.8° | 3375, 1640, 1160, 1075, 1045, 1020, 985 |
| Gynosaponin F | 191–193 | $C_{54}H_{92}O_{22} \cdot 3H_2O$ | 56.52 | 8.61 | 56.31 | 8.86 | +7.76° | (c=1.7) | +89.0° | 3375, 1635, 1165, 1070, 1040, 1015, 985 |
| Gynosaponin G | 192–194 | $C_{54}H_{92}O_{21} \cdot 3H_2O$ | 57.33 | 8.73 | 57.11 | 8.77 | +1.63° | (c=2.0) | +18.4° | 3375, 1640, 1155, 1065, 1045, 1015, 985 |

TABLE 1-continued

| | mp(°C.) | Formula | Elementary Analysis Calcd. C % | Calcd. H % | Found C % | Found H % | $[\alpha]_D^{22°}$ MeOH | Rotation | $[M]_D$ | IR |
|---|---|---|---|---|---|---|---|---|---|---|
| Gynosaponin I | 183–185 | $C_{47}H_{80}O_{17}\cdot 3H_2O$ | 58.13 | 8.93 | 57.77 | 8.77 | +14.2° | (c=1.5) | +138° | 3375, 1635, 1160, 1075, 1035, 1015, 990 |
| Gynosaponin J | 189–191 | $C_{48}H_{82}O_{17}\cdot 4H_2O$ | 57.47 | 9.04 | 57.58 | 8.92 | +13.3° | (c=1.5) | +133° | 3375, 1640, 1160, 1070, 1040, 1015, 990 |
| Gynosaponin K | 187–189 | $C_{48}H_{82}O_{17}\cdot 3H_2O$ | 58.52 | 9.00 | 58.41 | 8.89 | +13.4° | (c=1.8) | +132° | 3375, 1635, 1165, 1070, 1045, 1020, 990 |
| Gynosaponin M | 158–160 | $C_{41}H_{70}O_{12}\cdot 3/2H_2O$ | 62.97 | 9.40 | 63.20 | 9.60 | +25.7° | (c=1.0) | +201° | 3375, 1635, 1165, 1075, 1040, 1015, 990 |
| Gynosaponin N | 165–167 | $C_{42}H_{72}O_{12}\cdot 2H_2O$ | 62.66 | 9.52 | 62.89 | 9.81 | +25.0° | (c=1.3) | +201° | 3375, 1635, 1165, 1065, 1040, 1025, 985 |
| Gynosaponin O | 202–205 | $C_{60}H_{102}O_{27}\cdot 4H_2O$ | 54.28 | 8.35 | 54.28 | 8.30 | −1.31° | (c=2.5) | −17.4° | 3375, 1640, 1160, 1070, 1040, 1015, 980 |
| Gynosaponin P | 206–209 | $C_{54}H_{92}O_{28}$ | 58.46 | 8.36 | 58.26 | 8.42 | +8.27° | (c=2.5) | +91.7° | 3375, 1640, 1160, 1070, 1040, 1020, 980 |
| Gynosaponin Q | 180–182 | $C_{52}H_{88}O_{21}\cdot 5H_2O$ | 54.82 | 8.67 | 54.84 | 8.66 | +1.36° | (c=0.55) | +15.5° | 3375, 1635, 1160, 1070, 1035, 1010, 975 |
| Gynosaponin R | 195–197 | $C_{53}H_{90}O_{21}\cdot 3H_2O$ | 56.97 | 8.66 | 57.09 | 8.71 | +0.39° | (c=2.9) | +4.36° | 3375, 1635, 1160, 1070, 1040, 1015, 990 |
| Gynosaponin S | 179–181 | $C_{48}H_{82}O_{18}\cdot 4H_2O$ | 56.56 | 8.90 | 56.48 | 8.72 | +20.6° | (c=1.4) | +210° | 3375, 1635, 1160, 1070, 1035, 1015, 990 |
| Gynosaponin T | 177–179 | $C_{60}H_{102}O_{28}\cdot 3H_2O$ | 54.37 | 8.21 | 54.55 | 8.19 | −2.69° | (c=1.3) | −35.7° | 3375, 1635, 1160, 1070, 1040, 1015, 980 |
| Gynosaponin U | 151–153 | $C_{41}H_{70}O_{13}\cdot 3/2H_2O$ | 61.71 | 9.22 | 61.62 | 9.19 | +16.3° | (c=2.0) | +130° | 3375, 1635, 1160, 1070, 1040, 1020, 990 |
| Progynosapogenin $A_2$ | 188–190 | $C_{54}H_{92}O_{22}\cdot H_2O$ | 58.36 | 8.53 | 58.32 | 8.60 | +4.24° | (c=1.5) | +47.1° | 3375, 1635, 1165, 1075, 1035, 1015, 990 |
| Progynosapogenin A-AH | 183–185 | $C_{48}H_{82}O_{17}\cdot H_2O$ | 60.74 | 8.92 | 60.38 | 9.06 | — | | — | 3375, 1635, 1160, 1070, 1040, 1020, 980 |
| Progynosapogenin $O_1$ | 167–169 | $C_{36}H_{62}O_9\cdot H_2O$ | 65.82 | 9.82 | 66.05 | 9.85 | +31.7 | (c=2.9) | +20.8° | 3375, 1640, 1150, 1075, 1035, 1015, 990 |

TABLE 2

PMR Spectral Data

| | Methyl | C-24H | Anomeric Proton |
|---|---|---|---|
| Gynosaponin A | (I) 0.81s,0.91s,0.96s,1.05s 1.59d 1.26s,1.62s,1.62s,1.65s (J=5) | * | 4.81d, 4.99d, 5.06d, 5.27d, 5.38s (J=7) (J=7) (J=7) (J=7) |
| | (II) 0.79s,0.95s,0.95s,1.04s 1.59d 1.22s,1.61s,1.66s,1.69s (J=5) | * | 4.73d, 4.85d, 4.99d, * (J=7) (J=7) (J=7) |
| Gynosaponin B | (I) 0.83s,0.90s,0.98s,1.07s 1.62d,1.62d 1.28s,1.59s,1.67s,1.69s (J=5) (J=5) | 5.30m | 4.86d, 5.10d, 5.34d, 5,38s, 5.42s (J=7) (J=7) (J=7) |
| | (II) 0.81s,0.97s,0.97s,1.05s 1.61d,1.61d 1.24s,1.58s,1.69s,1.71s (J=5) (J=5) | * | 4.84d, 5.05d, 5.33d, 5,34d, 5.38s (J=7) (J=7) (J=7) |
| Gynosaponin E | (I) 0.83s,0.92s,0.98s,1.07s 1.60d 1.26s,1.57s,1.66s,1.68s (J=5) | 5.30m | 4.85d, 5.05d, 5.27d, 5.31s (J=6.5) (J=7.5) (J=7) |
| | (II) 0.79s,0.96s,0.96s,1.04s 1.58d 1.21s,1.56s,1.69s,1.71s (J=5) | * | 4.91d, 5.10d, 5.34d, 5.37s (J=6.5) (J=7.5) (J=7) |
| Gynosaponin F | (I) 0:82s,0.92s,0.96s,1.08s 1.63d 1.29s,1.62s,1.62s,1.62s (J=6) | 5.30m | 4.86d, 5.15d, 5.33d, 5.42s (J=7) (J=7) (J=7) |
| | (II) 0.78s,0.96s,0.96s,1.06s 1.63d 1.24s,1.60s,1.66s,1.67s (J=6) | * | 4.83d, 5.13d, 5.30d, 5.40s (J=7) (J=7) (J=7) |
| Gynosaponin G | (I) 0.82s,0.90s,0.97s,0.97s 1.62d,1.62d 1.30s,1.59s,1.65s,1.69s (J=6) (J=6) | 5.30m | 4.88d, 5.09d, 5.37d, 5.50s (J=7) (J=7) |
| | (II) 0.80s,0.97s,0.97s,0.97s 1.61d,1.61d 1.29s,1.58s,1.69s,1.71s (J=6) (J=6) | * | 4.85d, 5.05d, 5,34s, * (J=7) (J=7) |
| Gynosaponin I | (I) 0.83s,0.98s,0.98s,0.98s 1.28s,1.63s,1.65s,1.66s | 5.31m | 4.87d, 4.92d, 5.06d (J=7) (J=6.5) (J=7.5) |
| | (II) 0.78s,0.96s,0.96s,0.96s 1.25s,1.61s,1.71s,1.71s | * | 4.78d, 4.86d, 5.05d (J=7) (J=7) (J=7) |
| Gynosaponin J | (I) 0.83s,0.93s,0.97s,0.97s 1.59d 1.27s,1.57s,1.65s,1.68s (J=5) | 5.30m | 4.87d, 5.05d, 5,34s (J=7.5) (J=7.5) |

TABLE 2-continued

PMR Spectral Data

| | | Methyl signal / (Methyl) | C-24H | Anomeric Proton |
|---|---|---|---|---|
| | (II) | 0.78s,0.94s,0.94s,0.94s 1.53d<br>1.22s,1.51s,1.69s,1.69s (J=5) | * | 4.77d, 5.03d, 5.33s<br>(J=7.5) (J=7.5) |
| Gynosaponin K | (I) | 0.81s,0.92s,0.95s,0.95s 1.60d<br>1.28s,1.57s,1.62s,1.62s (J=5) | 5.22m | 4.83d, 5.10d, 5.42s<br>(J=7.5) (J=7.5) |
| | (II) | 0.77s,0.94s,0.94s,0.94s 1.57d<br>1.25s,1.57s,1.66s,1.66s (J=5) | * | 4.79d, 5.05d, *<br>(J=7.5) (J=7.5) |
| Gynosaponin M | (I) | 0.91s,0.96s,1.01s,1.03s<br>1.22s,1.53s,1.63s,1.65s | 5.33m | 4.96d, 5.08d<br>(J=7) (J=7) |
| | (II) | 0.84s,0.96s,0.99s,0.99s<br>1.19s,1.53s,1.64s,1.68s | 5.32m | 4.86d, 5.05d<br>(J=7) (J=7) |
| Gynosaponin N | (I) | 0.92s,0.92s,1.03s,1.03s 1.62d<br>1.22s,1.59s,1.65s,1.69s (J=5) | 5.33m | 5.09d, 5.38s<br>(J=7) |
| | (II) | 0.85s,0.94s,0.97s,1.00s 1.60d<br>1.19s,1.58s,1.67s,1.71s (J=5) | 5.30m | 5.04d, 5.34s<br>(J=7.5) |
| Gynosaponin O | (I) | 0.81s,0.87s,0.95s,1.06s 1.58d,1.60d<br>1.26s,1.58s,1.87s, (J=5) (J=5) | * | 4.84d, 5.08d, 5.32d, 5.36s, 5.42s<br>(J=7) (J=7) (J=7) |
| | (II) | 0.79s,0.94s,0.94s,1.03s 1.59d,1.59d<br>1.22s,1.55s,1.87s (J=5) (J=5) | * | 4.82d, 5.03d, 5.33d, 5.34s, 5.42s<br>(J=7) (J=7) (J=7) |

| | | Methyl signal | | Anomeric Proton |
|---|---|---|---|---|
| Gynosaponin P | (I) | 0.82s,0.91s,0.95s,1.07s 1.58d<br>1.26s,1.54s,1.86s (J=6) | | 4.88d, 5.10d, 5.32d, 5.36s<br>(J=7) (J=7) (J=7) |
| | (II) | 0.78s,0.94s,0.94s,1.04s 1.58<br>1.22s,1.58s,1.87s (J=6) | | 4.87d, 5.02d, * *<br>(J=7) (J=7) |
| Gynosaponin Q | (I) | 0.87s,0.98s,0.98s,1.10s<br>1.27s,1.63s,1.63s,1.67s | | 4.88d, 4.95d, 5.09d, 5.33d<br>(J=7) (J=7) (J=7) (J=7) |
| | (II) | 0.83s,0.96s,0.96s,1.07s<br>1.23s,1.64s,1.64s,1.69s | | 4.80d, 4.88d, 5.06d, *<br>(J=7) (J=7) (J=7) |
| Gynosaponin R | (I) | 0.87s,0.96s,0.98s,1.07s 1.57d<br>1.25s,1.60s,1.64s,1.68s (J=6) | | 4.80d, 5.06d, 5.27d, 5.35s<br>(J=6.5) (J=7) (J=7) |
| | (II) | 0.83s,0.96s,0.96s,1.05s 1.63d<br>1.22s,1.57s,1.66s,1.70s (J=6) | | 4.78d, 5.01d, 5.25d, *<br>(J=6.5) (J=7.5) (J=7) |
| Gynosaponin S | (I) | 0.82s,0.98s,0.98s,0.98s<br>1.25s,1.61s,1.63s,1.66s | | 4.79d, 5.03d, 5.10d<br>(J=7) (J=7) (J=7) |
| | (II) | 0.78s,0.97s,0.97s,0.97s<br>1.27s,1.63s,1.63s,1.68s | | 4.80d, 4.97d, 5.07d<br>(J=7) (J=7) (J=7) |
| Gynosaponin T | (I) | 0.82s,0.91s,0.95s,1.07s 1.58<br>1.27s,1.55s,1.85s (J=6) | | 4.83d, 5.03d, * 5.30d, 5.40s<br>(J=6.5) (J=7) (J=7) |
| | (II) | 0.80s,0.91s,0.91s,1.05s 1.58<br>1.24s,1.56s,1.85s (J=6) | | 4.82d, 4.98d, * * *<br>(J=7) (J=7) |
| Gynosaponin U | (I) | 0.91s,0.95s,1.00s,1.13s<br>1.22s,1.55s,1.87s | | 4.96d, 5.09d<br>(J=7.5) (J=7.5) |
| | (II) | 0.85s,0.95s,0.96s,1.01s<br>1.20s,1.57s,1.88s | | 4.88d, 5.05d<br>(J=7) (J=7) |

| | | Methyl | C-24H | Anomeric Proton |
|---|---|---|---|---|
| Progynosapogenin A$_2$ | (I) | 0.81s,0.94s,0.97s,0.97s 1.62d<br>1.30s,1.63s,1.63s,1.67s (J=5) | 5.33m | 4.88d, 5.04d, 5.11d, 5.48s<br>(J=7) (J=7) (J=7) |
| | (II) | 0.79s,0.97s,0.97s,0.97s 1.60d<br>1.27s,1.67s,1.71s,1.71s (J=5) | * | 4.85d, 4.94d, 5.09d, 5.38s<br>(J=7) (J=7) (J=7) |
| Progynosapogenin A-AH | (I) | 0.84s,0.96s,1.03s,1.09s 1.61d<br>1.29s,1.39s,1.64s,1.66s (J=6) | 5.30m | 4.88d, 5.36d, 5.44s<br>(J=7) (J=7) |
| | (II) | 0.82s,0.96s,1.04s,1.08s 1.61d<br>1.26s,1.39s,1.64s,1.66s (J=6) | * | 4.85d, * *<br>(J=7) |
| Progynosapogenin O$_1$ | (I) | 0.91s,0.95s,0.99s,1.04s<br>1.22s,1.53s,1.82s, | * | 5.17d<br>(J=7) |
| | (II) | 0.92s,0.96s,1.00s,1.05s<br>1.23s,1.54s,1.83s, | * | 5.17d<br>(J=7) |

(I) values in Py-d$_5$
(II) values in Py-d$_5$/D$_2$O
*chemical shifts are unclear due to overlapping of the signals.

The efficacy as an antitumorous drug of the saponin component isolated from Gynostemma pentaphyllum according to this invention will now be described with reference to examples of pharmacological tests and clinical cases. The term "saponin component" as hereunder used means a saponin mixture obtained in accordance with the procedures set forth in Example 18. In the clinical cases, the saponin component was used in the form of a powder prepared by adding nine times as much lactose.

1. Antiulcerous Action (1) Test on Action against an Ulcer Caused by Stress

A. Test Method

In accordance with the method proposed by Takagi et al. [K. Takagi and S. Akabe, Japan. J. Pharmacol., 18, 9 (1968)], male wister rats each weighing 200 g were placed in a stress box, and dipped breast-deep in a water tank at 23° C. for seven hours. After they were taken out of the water tank, each rat was killed, and its stomach was removed. 10 ml of a 0.5% formaldehyde solution were injected into the stomach of each rat. After 10 minutes, the stomach was incised along along its curvatura ventriculi major, and the gastric mucosa was examined.

The degree of ulceration was expressed by an ulcer factor obtained by measuring the length (mm) of each of the individual ulcers in each rat under a minimaster of 10 magnifications, and making a total of the ulcer lengths for each rat.

25 mg/kg or 100 mg/kg of the saponin component were orally administered to each group of rats, and 1.0 ml/kg of a physiological solution of sodium chloride was orally administered to the control group, half an hour before the rats were loaded with the stress. The average ulcer factor was compared between the groups of rats, and the rate of inhibition of ulceration caused by stress was determined for each group. The rate of inhibition was calculated in accordance with the following equation:

$$\text{Rate of inhibition (\%)} = \frac{\text{Average ulcer factor (Control Group)} - \text{factor (Test Group)}}{\text{Average ulcer factor (Control Group)}} \times 100$$

The test results are shown in Table 3.

B. Test Results

See Table 3 below.

TABLE 3

Degree of ulceration and rate of inhibition of ulceration by administration of the saponin component.

| | Ulcer factor (mm) | | |
|---|---|---|---|
| | Control group (1.0 ml/kg of | Test group | |
| Rat No. | physiological sodium chloride solution) | (25 mg/kg of saponin component) | (100 mg/kg of saponin component) |
| 1 | 17.15 | 15.20 | 8.70 |
| 2 | 16.50 | 13.95 | 9.55 |
| 3 | 20.70 | 16.20 | 11.25 |
| 4 | 21.15 | 16.40 | 14.00 |
| 5 | 24.30 | 14.65 | 16.55 |
| 6 | 18.80 | 17.26 | 14.40 |
| 7 | 20.25 | 14.70 | 10.70 |
| 8 | 19.80 | 15.65 | 12.04 |
| 9 | 22.60 | 15.10 | 12.57 |
| 10 | 19.55 | 14.55 | 9.70 |
| Average ulcer factor (mm) | 20.08 | 15.37 | 11.95 |
| Average rate of inhibition of ulceration (%) | 0 | 23.46 | 40.49 |

(2) Antiacetoulcerous Test

A. Test Method

Groups of 10 male wister rats each weighing about 200 g were each abdominally incised, after etherization, for exposure of the stomach. 0.05 ml of 10% acetic acid was injected under the serous membrane of the stomach, followed by suture, whereby ulceration was caused to take place. Starting on the third day after the incision, 25 mg/kg or 100 mg/kg of the saponin component were orally administered to the test group of rats once a day for five and 15 days continuously, while likewise, 1.0 ml/kg of a physiological solution of sodium chloride was orally administered to the control group. On the day immediately following the final administration, each rat was killed, and the stomach was removed therefrom. 10 ml of a 0.5% formaldehyde solution were injected into the stomach, and after 10 minutes, the stomach was incised along its curvatura ventriculi major. The longitudinal and transverse lengths of an ulcerated region were measured under a minimaster, and the area (mm) of the ulcerated region was obtained to indicate an ulcer index. The rate of curing (inhibition of ulceration) was calcuated in accordance with the following equation:

$$\text{Rate of curing (\%)} = \frac{\text{Average ulcer index (Control Group)} - \text{Average ulcer index (Test Group)}}{\text{Average ulcer index (Control Group)}} \times 100$$

The results of the five-day test and the 15-day test are shown in Tables 4 and 5, respectively.

B. Test Results

See Tables 4 and 5 below.

TABLE 4

Degree of ulceration and rate of curing by administration of the saponin component for five days.

| | Ulcer index (mm$^2$) | | |
|---|---|---|---|
| | Control group (1.0 ml/kg of | Test Group | |
| Rat No. | physiological sodium chloride solution) | (25 mg/kg of saponin component) | (100 mg/kg of saponin component) |
| 1 | 20.07 | 9.20 | 10.56 |
| 2 | 19.38 | 14.13 | 12.60 |
| 3 | 18.64 | 9.79 | 8.52 |
| 4 | 15.20 | 13.94 | 9.04 |
| 5 | 23.64 | 12.20 | 10.28 |
| 6 | 24.06 | 11.45 | 10.70 |
| 7 | 20.21 | 13.26 | 12.06 |
| 8 | 18.95 | 10.66 | 10.12 |
| 9 | 19.88 | 8.96 | 9.56 |
| 10 | 18.02 | 11.02 | 11.98 |
| Average ulcer index (mm$^2$) | 19.81 | 11.46 | 10.54 |
| Average rate of curing (%) | 0 | 42.15 | 46.79 |

TABLE 5

Degree of ulceration and rate of curing after administration of the saponin component for 15 days.

| | Ulcer index (mm$^2$) | | |
|---|---|---|---|
| | Control group (1.0 ml/kg of | Test group | |
| Rat No. | physiological sodium chloride solution) | (25 mg/kg of saponin component) | (100 mg/kg of saponin component) |
| 1 | 9.05 | 3.86 | 4.05 |
| 2 | 10.50 | 5.18 | 3.96 |
| 3 | 8.92 | 5.10 | 4.55 |
| 4 | 12.43 | 5.65 | 5.00 |
| 5 | 9.56 | 4.84 | 4.12 |
| 6 | 7.95 | 3.28 | 4.08 |
| 7 | 9.18 | 4.56 | 4.54 |
| 8 | 8.65 | 5.20 | 3.79 |
| 9 | 11.26 | 4.20 | 4.82 |
| 10 | 10.74 | 3.96 | 3.56 |
| Average ulcer index (mm$^2$) | 9.82 | 4.58 | 4.25 |
| Average rate of curing (%) | 0 | 53.36 | 56.72 |

As is noted from the foregoing results, the tests showed curing rates of 23.46% and 40.49% for ulcers caused by stress with the administration of the saponin component according to this invention in the amount of 25 mg/kg and 100 mg/kg, respectively, and 42.15%, 53.36%, 46.79% and 56.72% for ulcers caused by acetic acid with the administration of the saponin component in the amount of 25 mg/kg for five and 15 days, respectively, and 100 mg/kg for five and 15 days, respectively. It is, thus, obvious that the saponin component of this invention is highly effective against ulcers in the digestive organs.

(3) Clinical Cases

Case 1

Patient: Y. M., a 50-year-old housewife.
Disease: Gastric ulcer.
Family History: Her mother suffered from a gastric ulcer.
Past History: No particular disease.
Present Disease: About five months ago, she began to have a pain in the stomach, which was particularly acute when she was hungry. She often lost her appetite, and after she received treatment at another hospital in vain, she came to this hospital. X-ray and endoscopic examination led to the diagnosis of her case as a gastric ulcer.
Results of Treatment: 100 mg of the saponin component per days were internally administered between the meals every day for three months.
As the result, her subjective symptoms, such as a pain, were drastically improved, and X-ray and endoscopic examination showed virtually no ulcerated area in her stomach.

Case 2

Patient: S. K., a 34-year-old male company employee.
Disease: Duodenal ulcer.
Family History: His father died of a gastric cancer.
Past History: He had appendectomy when he was 20 years old.
Present Disease: About six months ago, he began to have an abdominal pain occasionally, which was acute particularly during the night. He began to have a pain almost every day one month ago, and visited this hospital. Upon X-ray examination, his case was diagnosed as a duodenal ulcer, and he was hospitalized.
Results of Treatment: 200 mg of the saponin component were orally administered every day for two months. As the result, X-ray examination ceased to show virtually any ulcerated area, and his subjective symptoms were improved to normal. He was, therefore, discharged from the hospital, and ordered to visit the hospital once a week.

Case 3

Patient: H. T., a 40-year-old male company employee.
Disease: Gastric ulcer.
Family History: No disease in particular.
Past History: He was hospitalized for one month for autonomic ataxia when he was 32 years old.
Present Disease: He began to have a pain sometimes in the upper part of his stomach about six months ago. Two months ago, he began to have such a pain whenever he was hungry, and often lack appetite and vomit. He visited the hospital, and after X-ray and endoscopic examination, his case was diagnosed as a gastric ulcer.
Results of Treatment: 100 mg of the saponin component were orally administered every day for two months. As the result, X-ray and endoscopic examination showed a drastic improvement. He recovered from the disease almost completely, as he ceased to have a pain an vomit, and began to have a good appetite.

Attention is now directed to pharmacological tests and clinical cases for describing the action of the saponin component according to this invention for preventing the side effects of glucocorticoids.

2. Action for Preventing the Side Effects of Glucocorticoids

The side effects of the glucocorticoids, which are adrenocortical hormones, include atrophy of the adrenal glands, which is said to give rise to symptoms of a buffalo's neck, a moon face, or the like. Atrophy of the thymus and reduction of the plasma cortisol are also prominent side effects of glucocorticoids. Tests were conducted for ascertaining how effective the saponin component obtained from hydrangea bines would be for preventing the side effects of glucocorticoids.

(1) Effects on Atrophy of the Adrenal Glands, Atrophy of the Thymus and the Plasma Cortisol (a) Cases in which the administration of a glucocorticoid preceded that of the saponin component.

10 mg/kg of dexamethasone as a glucocorticoid were intraperitoneally injected in the form of a solution thereof in 1 ml of a physiological solution of sodium chloride into each of a group of 10 male SD rats (five weeks of age) weighing 140 g ±5 g once a day for 10 days continuously. Then, on the 11th day, it was started to inject intraperitoneally into each rat 10 mg/kg of the saponin component in the form of a solution thereof in 1 ml of a physiological solution of sodium chloride once a day for 10 days continuously. Each of other rats defining a control group was intraperitoneally given 1 ml/kg of a physiological sodium chloride solution, instead of the saponin component, once a day for 10 days continuously starting on the 11th day of the tests. No dexamethasone, saponin component or physiological sodium chloride solution was given to a third group of rats. Upon completion of the final administration, the rats were abdominally incised, and the weights of the adrenal glands and the thymus, and the quantity of the plasma cortisol were measured for each group of rats. The averages of the values obtained by measurement are shown in Table 6.

TABLE 6

|  | Group to which no drug was given | Control Group to which dexamethasone and physiological sodium chloride solution were given | Group to which dexamethasone and saponin component were given |
|---|---|---|---|
| Weight of the adrenal glands (mg) | 64 ± 2 | 23 ± 1 | 45 ± 2 |
| Weight of the thymus (mg) | 286 ± 9 | 172 ± 13 | 214 ± 10 |
| Plasma cortisol (μg/dl) | 74 ± 2 | 30 ± 3 | 62 ± 2 |

The values thus obtained were used for calculation of the rate of atrophy of the adrenal glands and the thymus, and the rate of reduction of the plasma cortisol in accordance with the following equations:

$$\text{Rate of atrophy of the organ} = \frac{\text{Weight of the organ to which no drug was given} - \text{Weight of the organ to which the drugs were given}}{\text{Weight of the organ to which no drug was given}} \times 100$$

$$\text{Rate of reduction of plasma cortisol} = \frac{\text{Quantity of plasma cortisol in the group to which no drug was given} - \text{Quantity of plasma cortisol in the group to which the drugs were given}}{\text{Quantity of plasma cortisol in the group to which no drug was given}} \times 100$$

The results are shown in Table 7.

TABLE 7

|  | Control group to which dexamethasone and physiological sodium chloride solution were given | Group to which dexamethasone and saponin component were given |
|---|---|---|
| Rate of atrophy of the adrenal glands (%) | 64.1 | 29.7 |
| Rate of atrophy of the thymus (%) | 39.9 | 25.2 |
| Rate of reduction of plasma cortisol (%) | 59.5 | 16.2 |

(b) Cases in which the administration of the saponin component preceded that of a glucocortiocoid.

10 mg/kg of the saponin component were intraperitoneally injected in the form of a solution thereof in 1 ml. of a physiological solution of sodium chloride into each of a group of 10 male SD rats (five weeks of age) weighing 140 g ±5 g once a day for 10 days continuously. Each of other rats defining a control group was intraperitoneally given 1 ml/kg of a physiological sodium chloride solution once a day for 10 days continuously. Then, on the 11th day, it was started to inject 10 mg/kg of dexamethasone intraperitoneally into each of the two groups of rats once a day for 10 days continuously. No dexamethasone, saponin component or physiological sodium chloride solution was given to a third group of rats. Upon completion of the final administration, the rats were abdominally incised, and the weights of the adrenal glands and the thymus, and the quantity of the plasma cortisol were measured for each group of rats. The averages of the values obtained by measurement as shown in Table 8.

TABLE 8

|  | Group to which no drug was given | Control Group to which dexamethasone and physiological sodium chloride solution were given | Group to which dexamethasone and saponin component were given |
|---|---|---|---|
| Weight of the adrenal glands (mg) | 69 ± 2 | 20 ± 1 | 55 ± 2 |
| Weight of the thymus (mg) | 290 ± 10 | 165 ± 8 | 221 ± 10 |
| Plasma cortisol (μg/dl) | 71 ± 2 | 28 ± 1 | 57 ± 3 |

The values thus obtained were used for calculation of the rates of atrophy of the adrenal glands and the thymus, and the rate of reduction of the plasma cortisol as hereinabove set forth at (a). The results are shown in Table 9.

TABLE 9

|  | Control group to which dexamethasone and physiological sodium chloride solution were given | Group to which dexamethasone and saponin component were given |
|---|---|---|
| Rate of atrophy of the adrenal glands (%) | 71.0 | 20.3 |
| Rate of atrophy of the thymus (%) | 43.1 | 23.8 |
| Rate of reduction of plasma cortisol (%) | 60.6 | 19.7 |

As is obvious from the results shown above, the saponin component is highly effective for inhibiting the reduction in weight of the adrenal glands and the thymus due to their atrophy, and the reduction of the plasma cortisol, which are all caused by glucocorticoids. The efficacy of the saponin component was manifested even in the case where it was administered before the glucocorticoid. This fact indicates that the saponin component of this invention is not only effective for recovering the organs from the side effects of glucocorticoids, but also for preventing occurrence of any such side effect. As is noted from the foregoing description at (a), the rate of atrophy of the adrenal glands caused when 10 mg/kg of dexamethasone per day were intraperitoneally given for 10 days continuously, and amounting to about 64% could be lowered to 29.7%, i.e., less than a half by the administration of the saponin component, and likewise, the rate of atrophy of the thymus from about 40% to about 25%, and the rate of reduction of the plasma cortisol from about 60% to one-fourth, or about 16%. Substantially the same results could be obtained even when the saponin component was administered prior to the glucocorticoid as described at (b). More specifically, the atrophy of the adrenal glands could be reduced from about 70% to about 20%, the atrophy of the thymus from about 43% to about 24%, and the reduction of the plasma cortisol from about 60% to about 20%.

(2) Clinical Cases

Case 1

Patient: U.K., a 29-year-old male government employee.

Disease: Chronic nephrosis type nephritis, and a moon face caused by administration of a glucocorticoid (steroid).

Family History: His elder brother died of chronic hepatitis.

Past History: No disease in particular.

Present Disease: Three years ago, he was hospitalized for medical treatment, as his case was diagnosed as chronic nephrosis type nephritis. After 2 mg of an adrenocortical glucocorticoid, i.e., linderon per day were orally administered for three months continuously, he became obese with a moon face, and had languor in his whole body and palpitation. Therefore, the amount of the glucocorticoid was reduced to 1 mg per day, but its side effects were not improved at all. Recently, he even began to feel dizzy and nervous, and became sleepless.

Present Condition- Moon face (+); slightly red cheeks; volume of urine, 500 ml/day; blood pressure, 154/95 mm Hg. Kidney function tests - Serum cholesterol, 470 mg/dl; urea nitrogen, 30 mg/dl; urine protein (—); erythrocyte (+); nothing wrong elsewhere.

Results of Treatment: The saponin component began to be administered in the amount of 100 mg per day, while the oral administration of 1 mg of the glucocorticoid per day was continued. After three months, the kidney function tests showed a remarkable improvement; therefore, the administration of the glucocorticoid was discontinued, and the oral administration of the saponin component alone was continued for three more months in the amount of 100 mg per day. After the three months, all of his moon face, cheek, redness, dizziness, irritation and sleeplessness disappeared. The volume of his urine increased to 1,500 ml per day. At that time, the kidney function tests indicated complete recovery in all respects; i.e., serum cholesterol, 112 mg/dl; urea nitrogen, 11 mg/dl; urine protein ($\pm$); erythrocyte (—); and blood pressure, 122/80 mm Hg. Remarks: As the glucocorticoid (linderon) used for curing chronic nephrosis type nephritis produced the side effects which were too serious to be improved easily, the saponin component was administered with the glucocorticoid. As a result, it became possible to continue using the glucocorticoid safely without any further progress of the side effects, and the purpose of the treatment could be achieved in a short time. Still continued administration of the saponin component prepared from hydrangea bines led to complete elimination of the side effects of the glucocorticoid. No rebound or withdrawal phenomenon was observed when the administration of the glucocorticoid was discontinued.

Case 2

Patient: O. Y., a 52-year-old male company officer.

Disease: Chronic active hepatitis, and difficulty in steroid separation.

Family History: No disease in particular.

Past History: No disease in particular.

Present Disease: Five years ago, he began to be treated for chronic hepatitis. After he received various kinds of treatment in vain, he started to take orally prednisolone, an adrenocortical glucocorticosteroid hormone, in the amount of 15 mg per day two years ago. After three months, he had a moon face and a buffalo's neck. A reduction in the amount of the steroid caused him to have languor in his whole body and vomit, and these conditions were recovered when the amount of the steroid was restored to the original level. In other words, it became difficult for him to discontinue the use of the steroid. Accordingly, the amount of the steroid was not reduced despite its side effects, and its side effects became more prominent. Recently, he became to show a decrease in the volume of his urine, feel thirsty, and have a feeling of fatigue and palpitation.

Present Conditions - Moon face (+); buffalo's neck (+); somewhat red face; vascular trouble (+). Liver function tests - S. GOT 245 U/L; S. GPT 285 U/L; T.T.T. 15.3 U/L; 2 T.T. 20.3 U/L; $\gamma$-globulin, 29.4%; and no other abnormality. The biological examination of the liver confirmed the case as being of chronic active type. Results of Treatment: The saponin component was administered in the amount of 100 mg per day, while the oral administration of prednisolone was continued in the amount of 15 mg per day. After one month, the moon face and the buffalo's neck were somewhat improved, and he ceased to have any thirst, feeling of fatigue or palpitation. After three months, all of his subjective and objective symptoms disappeared, and he recovered his health. He showed a drastic improvement in liver function tests: S. GOT, 42; S. GPT, 34; T.T.T., 10.1; 2 T.T., 11.3; and $\gamma$-globulin, 24.3. Therefore, the administration of prednisolone was discontinued. No rebound or withdrawal phenomenon was found. For three months thereafter, he has not complained of any subjective or objective symptom; and the liver function tests indicate perfectly normal results, i.e., S. GOT, 24; S. GPT, 27; T.T.T., 4.31; 2 T.T., 7.4; and $\gamma$-globulin, 20.3.

Remarks: The use of the saponin component prepared from hydrangea bines, while the administration of the steroid was continued, led to elimination of the side effects, and difficulty involved in the discontinuation of use of the steroid in a short time without appearance of any rebound or withdrawal phenomenon.

Case 3

Patient: T. T., a 44-year-old housewife.

Disease: Chronic articular rheumatism, and difficulty in discontinuation of use of steroid.

Family History: Her father suffered from chronic articular rheumatism.

Past History: No disease in particular.

Present Disease: After his case was diagnosed as chronic articular rheumatism five years ago, she was treated in various ways, but continued to complain of an acute pain and heavy swelling. Therefore, she started the oral use of a steroid, i.e., prednisolone in the amount of 10 mg per day three years ago. After five months, she had a moon face, and came to feel tired in her whole body and dizzy, and suffer from oliguria. As the discontinuation of use of the steroid resulted in oppression in the chest and an attack of fever, the administration of prednisolone has been continued to date in the amount of 10 mg per day.

Present Conditions—Moon face (+); buffalo's neck (+); red cheeks (+); RA (+); CRF (+); blood sedimentation, 70 mm (one hour) and 124 mm (two hours); deformation of the knee, hand, leg and finger joints (+).

Results of Treatment: The saponin component prepared from hydrangea bines was given to the patient in the amount of 100 mg per day, while the oral use of prednisolone in the amount of 10 mg per day was continued. After two months, her moon face was improved, and her subjective and objective symptoms remarkably improved; therefore, the use of prednisolone was discontinued, while the oral administration of the saponin component was continued in the amount of 10 mg per day. No rebound or withdrawal phenomenon was found. After four months, the side effects of prednisolone disappeared completely.

Her articular pain and swelling were, however, worsened after the use of the steroid was discontinued.

Remarks: The side effects of the steroid used for a prolonged time for curing articular rheumatism could be eliminated by the use of the saponin component, and the difficulty involved in discontinuation of use of the steroid could also be overcome in a short time.

The antitumorous (and anticencerous) action of the saponin component according to this invention will now be described with reference to the results of pharmacological tests and clinical cases.

3. Antitumorous Action

(1) Tumor Weight Method

A. Test Method

Sarcoma 180 cells were transplanted into ddy type mice, and the saponin component prepared from hydrangea bines was given to them for seven days. On the 12th day, the tumorous sarcomas were taken out, and their weights were compared with those of the tumors removed from a control group of mice. The weights of the tumors taken out of the mice to which 50 mg/kg of the saponin had been orally given showed a reduction of about 40% as compared with the control group. Thus, the efficacy of the saponin component was ascertained, as a significant difference could be clearly recognized with the value of P being less than 0.05. The details of the tests will hereunder be described.

The tests were conducted with several groups each consisting of 10 female ddy type mice (six weeks of age) weighing 18 to 22 g. A hypodermically transplanted sarcoma 180 was extracted from another mouse, and washed with a physiological solution of sodium chloride containing Kanamycin. Sections having a diameter of 1.5 to 2.5 mm and containing $1 \times 10^6$ cells were prepared from the non-blood portion of the sarcoma, and transplanted hypodermically under the right armpit of each mouse by using a transplantation needle. After 24 hours following the transplantation, the saponin component in the amount of 10 mg/kg, 50 mg/kg or 500 mg/kg was injected intraperitoneally into each group of mice once a day in the form of a solution in a physiological solution of sodium chloride. The oral administration of the saponin component was performed by means of a gastric catheter after it was dissolved in purified water. A physiological solution of sodium chloride was given to the control group of mice under the same conditions as hereinabove described. The administration was continued for seven days. On the 12th day, the weight of the tumor (sarcoma) formed in each mouse was measured, and a ratio in the average tumor weight of each group of mice to the control group (T/C) was calculated, whereby the efficacy of the saponin component was evaluated.

B. Test Results

See Table 10.

TABLE 10

| Amount of the saponin component used (mg/kg/day) | Number of mice | Tumor weight (g) (average value ± standard deviation) | T/C | P< |
|---|---|---|---|---|
| Control Group | 10 | 2.75 ± 0.91 | 1.00 | |
| 10 mg (intraperitoneally) | 10 | 3.35 ± 1.40 | 1.22 | N.S. |
| 50 mg (intraperitoneally) | 10 | 1.71 ± 0.73 | 0.62 | 0.05 |
| 50 mg (orally) | 10 | 1.49 ± 0.88 | 0.54 | 0.05 |
| 500 mg (orally) | 10 | 2.09 ± 0.90 | 0.76 | N.S. |

[Notes]
(1) T/C: Average tumor weight ratio (i.e., ratio in average tumor weight of each group of mice to the control group);
(2) N.S.: No significant difference at P>0.05.

As is obvious from the results shown above, the use of the saponin component in the amount of 50 mg/kg showed an inhibition rate of 46% against an increase of tumor weight when it was orally administered, and 38% when it was intraperitoneally injected; therefore, the use of 50 mg/kg, whether orally or intraperitoneally, showed a higher rate of inhibition than 24% when a 10 times greater amount of 500 mg/kg was used. And it is noted that oral administration is more effective than intraperitoneal injection. Similar results could be obtained from the tests conducted by reducing the number of the transplanted tumorous cells to one-fifth, i.e., $2 \times 10^5$, and administering the saponin component for a longer period of 12 days. These results teach that the saponin component is effective for inhibiting an increase of tumor without showing a dose response, and that it is more effective when orally administered.

(2) Life Prolongation Test

A. Test Method

Sarcoma 180 was intraperitoneally transplanted into ddy type mice, and the saponin component prepared from hydrangea bines was orally given to the mice for 10 days. The mice were compared in the number of days of survival with those of the control group, whereby the life prolongation effect of the saponin component was examined. The control group showed an average survival period of 14.1 days, and the mice to which the saponin component has been given in the amount of 50 mg/kg showed an average survival period of 19.6 days. The results clearly indicated the life prolongation effect of the saponin component. The life prolongation effect of the saponin component on rats was tested in such a manner that the saponin component was orally given to the rats every day in the amount of 50 mg/kg for 10 days, and Yoshida sarcoma was then intraperitoneally transplanted into the rats, followed by comparison of the average survival period of the rats with that of the control group to which no saponin component had been given. While the control group showed an average survival period of 11 days, the rats to which the saponin component had been given showed an average survival period of 24.5 days clearing indicating the life prolongation effect of the saponin component. The details of the tests will hereunder be described.

Sections of sarcoma 180 ($1 \times 10^6$ cells), which had been prepared as described at (1) above, were intraperitoneally transplanted into several groups each consisting of 10 male ddy type mice (six weeks of age). After 24 hours, it was started to give each group of mice the saponin component prepared from hydrangea bines in the amount of 10 mg/kg or 50 mg/kg once a day for 10 days continuously by means of a gastric catheter after it had been dissolved in purified water. Only the same quantity of purified water was given to the control group of mice. Thus, the period and rate of survival of each group of mice after the transplantation were examined. As the use of the saponin component in the amount of 50 mg/kg produced the best results, the tests were then conducted with male wister rats each weighing about 200 g. The saponin component was orally administered to the rats in the amount of 50 mg/kg every day for 10 days continuously. After three days, Yoshida sarcoma ($5 \times 10^5$ cells) was intraperitoneally transplanted into the rats, and the period of their survival thereafter was examined.

B. Test Results

See Tables 11 and 12.

TABLE 11

Antitumorous effect of the saponin component on sarcoma 180 (mice).

| Amount of the saponin component used | Number of mice | Average period of survival (days) | Rate of death |
|---|---|---|---|
| Control Group | 10 | 14.1 | 10/10 |
| 10 mg | 10 | 16.5 | " |
| 50 mg | 10 | 20.0 | " |
| 500 mg | 10 | 18.1 | " |

TABLE 12

Antitumorous effect of the saponin component on Yoshida sarcoma when the saponin component was given beforehand.

| Amount of the saponin component used | Number of rats | Average period of survival (days) | Rate of death |
|---|---|---|---|
| Control Group | 10 | 11.0 | 10/10 |
| 50 mg | 10 | 27.5 | " |

(3) Clinical Cases

Case 1

Patient: A. S., a 49-year-old female company employee.
Disease: Hepatom.
Family History: No particular disease.
Past History: No particular disease.
Present Disease: Two months ago, she complained of a pain and discomfort in the right costal region. Her case was diagnosed as hepatom. She did not get better despite the treatment. As she gradually came to feel languid, and lose her appetite and weight, she visited the hospital. She was of average build, and somewhat undernourished. The skin showed an icteric yellow tint. Several somewhat hard and uneven masses of thumb-ball size were palpable three fingerbreadths below the right costal margin. Abdominal dropsy was recognized. Erythrocyte count, 2,200,000/mm$^3$; leukocyte count, 1,100/mm$^3$; blood sedimentation, 50 mm (one hour); blood platelets, 50,000/mm$^3$; urine bilirubin (+); occult blood test for feces (+); GOT/GPT, 5.0; A/G, 0.50; α-fetoprotein, 2,000 μg/dl. A scintigram of the liver showed a filling defect.
Results of Treatment: 200 mg of the saponin component prepared from hydrangea bines were orally given in two portions every day for one month continuously. Her languor, lack of appetite and icterus disappeared. The abdominal dropsy ceased to be recognized. The swelling of the liver was reduced to one fingerbreadth with a reduction in the size of the masses. The laboratory studies revealed the following values: erythrocyte count, 3,100,000/mm$^3$; leukocyte count, 10,000/mm$^3$; blood sedimentation, 40 mm (one hour); blood platelets, 82,000/mm$^3$; absence of bilirubinuria; occult blood test for feces (−); GOT/GPT, 4.0; A/G, 0.8; α-fetoprotein, 1,500 μg/dl.

These values represented substantially normal results. After four months, no subjective or objective symptom. The liver was palpable one fingerbreadth below the costal margin, and though it was slightly hard, it was smooth, and no tumorous mass was palpable. All the abdominal dropsy disappeared. Laboratory studies revealed normal results: erythrocyte count, 4,500,000/mm$^3$; leukocyte count, 7,900/mm$^3$; blood sedimentation, 25 mm (one hour); blood platelets, 150,000/mm$^3$; GOT/GPT, 1.5; A/G, 1.2; α-fetoprotein, 1,000 μg/dl. She was discharged from hospital, and has continued to take the saponin component orally two months now. It has become for her to engage in her usual work.

Case 2

Patient: M. M., a 61-year-old male company employee.
Disease: Carcinoma of the esophagus.
Family History: Her daughter was operated upon for uterine cancer.
Past History: No particular disease.
Present Disease: Six months ago, he began to have a feeling of obstruction and a pain when swallowing food. Upon medical examination, her case was diagnosed as a light one of cancer of the esophagus two months ago. He was treated by radiotherapy in vain, and visited this hospital. He was of average build, undernourished, and dry-skinned. X-ray examination of the esophagus revealed a stricture and a mass of low projection. The erythrocyte count was 2,500,00/mm$^3$, and the leukocyte count was 6,000/mm$^3$.
Results of Treatment: 200 mg of the saponin component prepared from hydrangea bines were orally administered in two portions every day for one month. The stricture and pain which he had been feeling when swallowing food were improved to some extent, and X-ray examination indicated the reduction in size of the mass of low projection. The erythrocyte count was 3,000,000/mm$^3$, and the leukocyte count was 6,000/mm$^3$. After six months of the use of the saponin component, he ceased to have a feeling of constriction and a pain when swallowing food, and X-ray examination of the esophagus confirmed recovery without showing any protuberance any longer. Both the erythrocyte and leukocyte counts were restored to their normal levels, i.e., 4,600,000/mm$^3$ and 7,500/mm$^3$, respectively. No recurrence or metastasis has been seen for six months.

Case 3

Patient C. A., a 55-year-old male company employee.
Disease: Ascites cancer.
Family History: No particular disease.
Past History: No particular disease.

Present Disease: He had his stomach excised for gastric cancer two years ago. One year ago, he began to have an abdominal distention and a tendency to vomit, and abdominal dropsy was recognized three months ago. He began to feel heavy in the left supraclavicular fossa and the left axilla, in which finger-tip and adzukibean sized tumorous masses were palpable, and came to this hospital. He was of average build, dry-skinned, and undernourished. Finger-tip and adzuki-bean sized metastasized tumors were recognized in the left supraclavicular fossa and the left axilla. The abdomen was distended and stored dropsy, and a tumor was palpable in the upper part of the abdomen. The erythrocyte count was 2,300,000/mm$^3$, and the leukocyte count was 3,300/mm$^3$.

Results of Treatment: 150 mg of the saponin component per day were orally administered in three portions. After one month, the abdominal dropsy was decreased, and virtually no swelling of the abdomen could be recognized.

The erythrocyte count was improved to 2,800,000/mm$^3$, and the leukocyte count to 4,500/mm$^3$. After five months of continuous use of the saponin component, all the abdominal dropsy disappeared, the skin became glossy, and a reduction was noticed in the size of the tumor in the upper part of the abdomen. Although there was no reduction in the size of the metastasized tumors in the left supraclavicular fossa and axilla, there was no worsening, as the pain was totally eliminated. The erythrocyte count was 3,100,000/mm$^3$, and the leukocyte count was 5,000/mm$^3$. He is still being treated with the saponin component, and making favorable progress toward recovery without showing any sign of worsening. This is an example in which the abdominal dropsy has been removed in a case of ascites cancer.

Attention is now directed to examples of pharmacological tests supporting the efficacy of the saponin component according to this invention as a cell activator (for preventing ageing, and relieving fatigue).

4. Cell Activating Action

(1) Cell Activation Test

It is well known that a cell is a basic unit for the life of a living body. The process of growth and degeneration of a cell can be studied if a cell is separated from the tissue of a living body, and multiplied by division in an appropriate culture medium, such as a MEM culture medium containing 10% of calf serum, for successive cultivation. The progress of successive cultivation can be divided into three periods, i.e., the first period during which the first generation is cultured, the second period during which multiplication takes place at a constant speed, and the third period during which the degree of multiplication shows a gradual decline until the cell finally dies out without being capable of succession, however carefully the conditions may be controlled. The second period is longer than the other two periods, and is a period during which the cells per se acquire a high power of protein synthesis, and an increased amount of DNA, and undergo active division at a constant speed. During the third period, the disintegration of ribosome takes place in the cell, resulting in reduction of its power of protein synthesis, and incapability of its succession, until finally the cell ends its life. The frequency of succession of a cell, which may be considered to mean the life of the cell, depends substantially on the type of the cell involved, if the same culture medium is used for cultivation. For example, a normal diplontic fibroblast (Wl-1) separated from the lung of a human foetus is multiplied by repeating division at a speed of 35±2 hours per division during the second period (period of multiplication) when cultivated in a MEM culture medium containing 10% of calf serum, and during the third period, it grows weak and dies out without being capable of any further succession after the 51st generation. A cell separated from the human skin showing Werner's syndrome dies out without being capable of further successive cultivation after the 22nd generation. In this connection, it has been found that if 200 μg/ml of the saponin component is added into the culture medium in the beginning of the second period, the activity of the cell is prolonged during the second period to thereby increase the frequency of successive cultivation. More specifically, the addition of the saponin component in the amount of 200 μg/ml resulted in realization of successive cultivation until the 27th generation, i.e., prolongation of the cell life by 22.7%. Likewise, the addition of the saponin component in the amount of 200 μg/ml into the culture medium for a normal diplontic fibroblast derived from the lung of a human foetus resulted in successive cultivation until the 59th generation, i.e., prolongation of the cell life by 15.7%. The cell activating action of the saponin component according to this invention will be described in further detail with reference to examples.

EXAMPLE 1

A tissue slice of the human skin showing Werner's syndrome was treated with a 0.05% aqueous solution of trypsin to form a cell suspension. The cell suspension was implanted into a MEM culture medium containing 10% of calf serum at a ratio of 1:4, and cultivation was conducted at 36° C. The term "MEM" stands for a "medium essential medium for suspension". In two or three days, the cells covered the whole glass surface. The cells were treated with trypsin again to form a cell suspension. The contents of a single culture bottle were divided into two portions, and incorporated into a MEM culture medium containing 10% of calf serum for successive cultivation. In a similar way, regular successive cultivation was repeated twice a week until the 22nd generation, whereafter the cells ceased to multiply themselves, and became incapable of any more successive cultivation (Control Example). Starting with the seventh generation, the saponin component was added into the culture solution in the amount of 200 μg/ml., and successive cultivation was continued in a similar way. Thus, the life of the cells could be prolonged remarkably with an increased frequency of successive cultivation as shown below, while in the event no saponin component was used, the successive cultivation of the cells ended with the 22nd generation.

TABLE 13

| Example | Frequency of successive cultivation (times) | Rate of prolongation of cell life (%) |
|---|---|---|
| Control | 22 | 0 |
| Invention (saponin added) | 27 | 22.7 |

EXAMPLE 2

The procedures of Example 1 were repeated for preparing a cell suspension from a normal diplontic fibroblast (WI-I) derived from the lung tissue of a human foetus. The cell suspension thus prepared was implanted into a MEM culture solution containing 10% of calf serum for successive cultivation. In a similar way, regular successive cultivation was repeated twice a week until the 51st generation, whereupon the cells ceased to multiply themselves any more, and became incapable of any more successive cultivation (Control Example). Starting with the 21st generation, the saponin component was added into the culture solution in the amount of 200 μg/ml., and successive cultivation was continued in a similar way. The successive cultivation could be continued until the 59th generation with an increase of 15.7% in the life of the cells.

TABLE 14

| Example | Frequency of successive cultivation (times) | Rate of prolongation of cell life (%) |
|---|---|---|
| Control | 51 | 0 |
| Invention (saponin added) | 59 | 15.7 |

[Note] MEM (Minimum Essential Medium for Suspension):

| | |
|---|---|
| L-Arginine hydrochloride | 126.4 mg/liter; |
| L-Cystine | 24.0 mg/liter; |
| L-Glutamine | 292.3 mg/liter; |
| L-Histidine hydrochloride | 41.9 mg/liter; |
| L-Isoleucine | 52.5 mg/liter; |
| L-Leucine | 52.5 mg/liter; |
| L-Lysine hydrochloride | 73.1 mg/liter; |
| L-Methionine | 14.9 mg/liter; |
| L-Phenylalanine | 33.0 mg/liter; |
| L-Threonine | 47.6 mg/liter; |
| L-Tryptophan | 10.2 mg/liter; |
| L-Tyrosine | 36.2 mg/liter; |
| L-Valine | 46.9 mg/liter; |
| L-Choline hydrochloride | 1.0 mg/liter; |
| D-Calcium pantothenate and | 1.0 mg/liter; |
| Folic acid | 1.0 mg/liter. |

(2) Fatigue Resistance Test

A. Test Method

Groups each consisting of 20 male dr type mice weighing 15 to 20 g were kept away from food and water for one hour, and the saponin component was orally given to each mouse in the amount of 50 mg/kg or 200 mg/kg in the form of an aqueous solution thereof. After one hour, a load weighing 3% of the weight of each mouse was attached to its tail, and the mouse was caused to swim in water at 22° C., whereby the length of time (seconds) for which the mouse could withstand the load and keep swimming was determined. Each mouse of the control group was caused to drink the corresponding amount of water. The fatigue limit for each mouse was when it sank under the water and could not raise its head above the water for at least 10 seconds.

TABLE 15

| Amount of the saponin component given | Number of mice | Duration to fatigue limit (seconds) (average ± standard deviation) |
|---|---|---|
| Control Group | 20 | 188 ± 10.3 |
| 50 mg/kg (orally) | 20 | 248 ± 13.9 |
| 200 mg/kg (orally) | 20 | 296 ± 16.3 |

As is obvious from the foregoing results, the saponin component serves to prolong significantly the length of time for which the mice can keep swimming, and has a fatigue resisting action.

The following description of pharmacological tests and clinical cases will illustrate the effectiveness of the saponin component according to this invention as a sedative, a hypnotic and an agent for controlling general malaise or stress.

5. Sedative and Hypnotic Action (1) Hypnotized Time Prolongation Test (Test for Action for Strengthening the Effect of a Barbital Salt)

A. Test Method

The saponin component was intraperitoneally injected into groups each consisting of 10 female ddy mice weighing 19 to 20 g in the amount of 50 mg/kg or 100 mg/kg in the form of a solution thereof in 1 ml. of a physiological sodium chloride solution. After half an hour, a sodium salt of barbital was intraperitoneally injected into each mouse in the amount of 300 mg/kg. A physiological solution of sodium chloride in the amount of 1 ml. was intraperitoneally injected into each mouse of the control group, followed after half an hour by intraperitoneal injection of sodium barbital in the amount of 300 mg/kg. The tests were conducted in accordance with the method of Kuhn et al. [W. L. Kuhn & E. F. Van Mannen, J. Pharm. Exp. Therap., 134, 60 (1961)].

B. Test Results

The mice to which the saponin component had been administered showed a longer average hypnotized time than those of the control group. It is noted that the saponin component strengthened the effect of the sodium barbital.

TABLE 16

| Amount of the saponin component | Number of mice | Hypnotized time (min.) (average ± standard deviation) | $P<$ |
|---|---|---|---|
| Control Group | 10 | 51.3 ± 6.3 | 0.01 |
| 50 mg/kg | 10 | 65.1 ± 2.8 | 0.01 |
| 100 mg/kg | 10 | 67.4 ± 3.3 | 0.01 |

As is noted from this table, the use of the saponin component in the amount of 50 mg/kg and 100 mg/kg could prolong the hypnotized time by about 27% and 31%, respectively. These results support the sedative action of the saponin component according to this invention, and the availability thereof as a hypnotic.

(2) Mescaline Test

This is one of the methods for testing the sedation of a particular drug. A mouse to which mescaline is given does a violent scratching motion by its hind legs, but stops that motion when it is given a drug having a sedative action.

A. Test Method

Mescaline in the amount of 50 mg/kg was intramuscularly injected into each member of groups each consisting of 10 ddy type mice weighing 19 to 20 g, followed after 15 minutes by intraperitoneal injection of the saponin component in the amount of 50 mg/kg or 100 mg/kg in the form of a solution thereof in 1 ml. of a physiological sodium chloride solution. Only a physiological sodium chloride solution in the amount of 1 ml. was intraperitoneally injected into each mouse of the control group. The number of the scratching motions by the hind legs of each mouse was recorded for 15 minutes, and compared with the results obtained on the control group, in accordance with the method of Ban et al. [Yoshio Ban et al., Method of Studying Medicines, 251, Asakura Shoten, Tokyo (1969)].

B. Test Results

The mice to which the saponin component prepared from hydrangea bines had been given showed a significantly smaller number of scratching motions than those of the control group, as shown in the table below.

TABLE 17

| Amount of the saponin component given | Number of mice | Number of scratching motions (average + standard deviation) | P< |
|---|---|---|---|
| Control Group | 10 | 45 ± 4 | 0.01 |
| 50 mg/kg | 10 | 21 ± 3 | 0.01 |
| 100 mg/kg | 10 | 17 ± 3 | 0.01 |

As is noted from the table, the use of the saponin component in the amount of 50 mg/kg and 100 mg/kg could reduce the scratching motion of the mice by 53% and 62%, respectively, relative to the frequency of the motion by those of the control group. These results support the sedative action of the saponin component according to this invention.

(3) Writhing Test by Acetic Acid

This is also a method used for testing the sedative and analgesic action of a particular drug. After the drug to be tested is given to a mouse, 0.7% acetic acid is intraperitoneally injected thereinto. The frequency at which the mouse writhes and twists its body is measured, and compared with the results obtained on a control. The lower frequency indicates the higher sedative and analgesic action of the drug.

A. Test Method

The saponin component in the amount of 50 mg/kg or 100 mg/kg was intraperitoneally injected into each member of groups each consisting of 10 male ddy type mice weighing 20 to 22 g in the form of a solution thereof in 1.0 ml. of a physiological sodium chloride solution. Only a physiological sodium chloride solution in the amount of 1.0 ml. was intraperitoneally injected into each mouse of the control group. After one hour, 0.7% acetic acid was intraperitoneally injected into each mouse, and immediately thereafter, it was started to count the number of times for which the mouse twisted its body during the period of 15 minutes.

B. Test Results

See Table 18.

TABLE 18

| Amount of the saponin component given | Number of mice | Number of times of twisting (average ± standard deviation) | P< |
|---|---|---|---|
| Control Group | 10 | 48.9 ± 6.9 | 0.01 |
| 50 mg/kg | 10 | 41.1 ± 7.7 | 0.01 |
| 100 mg/kg | 10 | 35.1 ± 6.5 | 0.01 |

As is obvious from the table, the use of the saponin component in the amount of 50 mg/kg and 100 mg/kg could significantly reduce the number of times for which the mice twisted their bodies, by about 16% and 28%, respectively, relative to the results obtained on the control group. The test results shown above clearly reveal the sedative action of the saponin component according to this invention.

(4) Stress Loading Test for Mice

A. Test Method

The saponin component in the amount of 50 mg/kg or 100 mg/kg per day was orally given to each member of groups each consisting of 10 male ddy type mice weighing 19 to 20 g in the form of a solution thereof in 1.0 ml. of a physiological sodium chloride solution for 10 days continuously. A physiological sodium chloride solution in the amount of 1.0 ml. per day was orally given to each mouse of a control group for 10 days. Stress was loaded on all the mice in accordance with the method of Takagi et al. [K. Takagi et al., Jap. J. Pharmac., 22, 17 (1972)]. The mice were placed in a stainless steel cage measuring 14 mm by 15 mm by 20 mm, and holding 10 g of sponge, and the cage was stirred at an amplitude of 12.8 cm and a stirring rate of 130 times per minute for 210 minutes, whereby all the mice were loaded with stress.

After one hour, the mice were placed on a stainless steel plate, and the plate was inclined at a rate of 105° per minute. In this way, the angle at which the mouse slid down the plate without being able to withstand the inclination any longer was determined, whereby the power of the saponin component for recovering the mice from stress was tested. One hour after the stirring of the cage was terminated, the temperature of the rectum of each mouse was measured, and the degree of its recovery from the stress was ascertained.

B. Test Results

While the mice of the control group slid down the plate at an average angle of 45° one hour after the termination of the stirring operation, the mice to which the saponin component had been given could withstand the inclination until a significantly greater angle, i.e., those to which 50 mg/kg of the saponin component had been given could withstand the inclination until an average of 51.2°, and those to which 100 mg/kg of the saponin component had been given, until an average of 52.3°.

While one hour after the termination of the stirring operation, the mice of the control group showed an average rectum temperature of 35.1° C., the mice to which the saponin component had been given in the amount of 50 mg/kg and 100 mg/kg showed a significantly faster rate of recovery to 36.0° C. and 36.2° C., respectively, on an average.

The four pharmacological tests as hereinabove described support the sedative, hypnotic and stress relieving action of the saponin component according to this invention.

(5) Clinical Cases

Case 1

Patient: Y. O., a 42-year-old housewife.
Disease: Insomnia.
Family History: Her mother was being treated for autonomic imbalance.
Past History: No particular disease.
Present Disease: One year ago, the patient suffered from insomnia for the first time, and after she took a tranquilizer in vain, she visited this hospital. She was of average build, and had an ordinary skin. A blood test did not disclose any abnormality in her liver or kidney function. C.M.I. was in the region III. The only symptom of which the patient was conscious was of insomina.

Results of Treatment: The saponin component in the amount of 200 mg per day was orally given to the patient in two portions every day for one month continuously. As the result, the C.M.I. was normalized into the region I, and she ceased to be sleepless. This is a case in which insomnia was cured in as short a time as one month. This result is considered to have been attributable to the action of the saponin component as a CNS depressant.

Case 2

Patient: O. M., a 29-year-old female keypuncher.
Disease: Syndrome of general malaise (headache and uneasiness).
Family History: No particular disease.
Past History: No particular disease.
Present Disease: She started to work as a keypuncher for a computer two years ago. She began to have a headache during work one year ago, and as it became particularly acute recently, she visited this hospital. She was of average build, and had an ordinary skin. A blood test did not reveal any abnormality. She was always conscious of uneasiness, and suffered from a headache as soon as she got to work. The C.M.I. was in the region II.
Results of Treatment: The saponin component in the amount of 200 mg per day was orally given to the patient in two portions evey day for one month continuously. As the result, the C.M.I. was normalized into the region I, and she ceased to suffer from a headache, and feel uneasy in her daily life. She came to feel comfortable during work.

Case 3

Patient: K. K., a 19-year-old female student.
Disease: Mental uneasiness and hysteria.
Family History: No particular disease.
Past History: She was operated upon for duodenal ulcer when she was 15 years old.
Present Disease: One year ago, she began to feel uneasy about her study, and always irritated. As she had a feeling of anxiety about anything, and came to say anything in a harsh manner, she visited this hospital. She was of small build, and had a skin of ordinary color. A blood test did not reveal any abnormality. She was always conscious of irritation and a feeling of anxiety. The C.M.I. was in the region II.
Results of Treatment: The saponin component in the amount of 200 mg per day was orally given to the patient in two portions every day for one month continuously. As a result, she ceased to feel irritated. After two months, her feeling of anxiety completely disappeared, and the C.M.I. was normalized into the region I. It became possible for her to live a normal daily life. This was a case in which the sedative action of the saponin component manifested itself.

Case 4

Patient: D. Y., a 39-year-old male company employee.
Disease: Autonomic imbalance (migraine, a sense of fatigue, lack of appetite, stiffness in the shoulders, cold hands and feet, and irritation).
Family History: No particular disease.
Past History: No particular disease.
Present Disease: One and a half years ago, the patient began to exhaust his nerves on his work, feel constantly irritated, have a migraine, lack appetite, feel stiff in his shoulders and very chilly in his hands and feet, and have a sense of fatigue. After he tried a tranquilizer in vain, he visited this hospital. He was of average build, and had a skin of ordinary color. Neither an X-ray examination nor a blood test disclosed any abnormality. He, however, complained strongly of various subjective symptoms, such as a migraine, lack of appetite, stiffness in the shoulders, chilly hands and feet, irritation and a sense of fatigue. The C.M.I. was in the region III.

Result of Treatment: The saponin component in the amount of 200 mg per day was orally given to the patient in two portions every day. After one month, he ceased to be conscious of the irritation, migraine and chill in the hands and feet of which he had mainly complained. The C.M.I. was normalized into the region II. After two and a half months, he recovered his appetite, ceased to have any stiffness in the shoulders, and was relieved from a sense of fatigue of which he had always been conscious. After the close of three months, the administration of the saponin component was discontinued, and after the expiration of six months, he is now living an ordinary daily life without any recurrence of the disease.

6. Lipid Metabolism Action

[Preparation of Fat Cells for Testing Purpose]

Fat tissues were separated from the epididymides of male wister rats weighing 150 to 180 g each, and fat cells were obtained therefrom in accordance with the Rodbell's method [M. Rodbell, J. Biol. Chem., 239, 375 (1964)]. A small section was prepared from 4 g of the fat tissue, and placed in 10 ml. of Krebs-Ringer bicarbonate buffer containing 0.4 g of albumin, 10 mg of collagenase and 5 mg of glucose, and having a pH value of 7.4. It was heated at 37° C. for 50 minutes, and subjected to centrifugal separation at 300 rpm, whereby a floating fat cell layer was separated. Added into the fat cell were 10 ml. of the aforesaid buffer (pH 7.4), and the solution was carefully stirred to wash the fat cell, followed by centrifugal separation at 300 rpm for 30 seconds. This procedure was repeated twice, whereby the fat cells were washed perfectly, and these fat cells were used for the tests. The tests were conducted with an aqueous solution of each of gynosaponins A, B, E, F, G, I, J, K, M, N, O, P, Q, R, S, T and U, and progynosapogenins $A_2$, A—AH and $O_1$, which had a pH value adjusted to 7.4.

(1) Effects of Gynosaponins on the Decomposition of the Fat in the Fat Cell by ACTH A. Test Method The fat cells obtained by treating with collagenase were suspended in Krebs-Ringer bicarbonate buffer (KRB) having a pH value of 7.4. Placed into a test tube were 0.3 ml. of the solution thus obtained (containing 100 mg of fat cells), 0.1 ml. of ACTH solution containing 1 μg of ACTH, 0.1 ml. of each saponin solution containing 500 μg of saponin, and 0.3 ml. of a 5% alubumin solution in KRB, and having a pH value adjusted to 7.4. They were heated at 37° C. for two hours, and the amount of the resulting free fatty acid was determined in accordance with the Dole's method [V. P. Dole, J. Biol. Chem., 35, 150 (1958)].

Namely, 3 ml. of Dole's extract were separated into the reaction system, and 1 ml. of a thymol blue solution was added thereinto. Nitrogen was blown into the resulting solution, and the solution was titrated with a 0.008 N aqueous solution of sodium hydroxide, while it was being stirred. The amount of the resulting free fatty acid was determined in accordance with a calibration curve.

The rate of inhibition against fat decomposition was obtained in accordance with the following equation:

$$\text{Rate of inhibition against fat decomposition (\%)} = \frac{A - B}{A} \times 100$$

wherein A stands for the amount of the free fatty acid formed by addition of ACTH along in the amount of 1 μg/ml.; and B stands for the amount of the free fatty acid formed by addition of ACTH and saponin in the amount of 1 μg/ml. and 20 μg/ml., respectively.

B. Test Results

Table 19 shows the rates of inhibition determined for the various gynosaponins as hereinabove described against the decomposition by ACTH of the fat in the fat cells.

TABLE 19

| Additive | Free fatty acid formed by decomposition of fat (μ Eq/g) | Rate of inhibition (%) |
|---|---|---|
| None | 0 | — |
| ACTH | 8.4 | 0 |
| ACTH + gynosaponin A | 6.1 | 27 |
| ACTH + gynosaponin B | 6.9 | 18 |
| ACTH + gynosaponin E | 5.9 | 30 |
| ACTH + gynosaponin F | 6.3 | 25 |
| ACTH + gynosaponin G | 5.8 | 31 |
| ACTH + gynosaponin I | 6.6 | 21 |
| ACTH + gynosaponin J | 5.3 | 37 |
| ACTH + gynosaponin K | 6.1 | 27 |
| ACTH + gynosaponin M | 6.4 | 24 |
| ACTH + gynosaponin N | 5.2 | 38 |
| ACTH + gynosaponin O | 5.6 | 33 |
| ACTH + progynosapogenin $A_2$ | 6.2 | 26 |
| ACTH + progynosapogenin A—AH | 6.3 | 25 |
| ACTH + progynosapogenin $O_1$ | 5.9 | 30 |
| ACTH + gynosaponin P | 6.6 | 21 |
| ACTH + gynosaponin Q | 5.8 | 31 |
| ACTH + gynosaponin R | 6.2 | 26 |
| ACTH + gynosaponin S | 5.4 | 36 |
| ACTH + gynosaponin T | 6.3 | 25 |
| ACTH + gynosaponin U | 5.6 | 33 |

[Note]
ACTH was used in the amount of 1 μg/ml. and the saponins in the amount of 20 μg/ml. in all cases where they were involved.

As is noted from this table, a free fatty acid in the amount of 8.4 μ Eq/g resulted from the decomposition of fat when the fat cells had been acted upon with ACTH in the amount of 1 μg/ml., and left to stand at 37° C. for two hours, but the use of the gynosaponins each in the amount of 20 μg/ml. restricted the decomposition of fat by ACTH, hence reducing the amount of the free fatty acid. The average rate of inhibition was 28%.

(2) Effects of Gynosaponins on the Decomposition by Adrenalin of the Fat in the Fat cells A. Test Method The fat cells obtained by treating with collagenase were suspended in Krebs-Ringer phosphate buffer (KRP) having a pH value of 7.4. Placed into a test tube were 0.3 ml. of the solution thus obtained, and containing 100 mg of fat cells, 0.1 ml. of an adrenalin solution containing 1 μg of adrenalin, 0.1 ml. of a saponin solution containing 20 μg of saponin, and 0.5 ml. of a 5% albumin solution in KRP, and having a pH value adjusted to 7.4. They were heated at 37° C. for two hours, and the amount of the resulting free fatty acid was determined in accordance with the Dole's method. More specifically, 3 ml. of Dole's extract were placed in the reaction system, and after they were shaked for five minutes, 3 ml. of heptane were dispensed, and 1 ml. of a thymol blue solution was added thereinto. The resulting solution was titrated with a 0.008 N aqueous solution of sodium hydroxide, while it was being stirred with nitrogen, and the amount of the resulting free fatty acid was determined in accordance with a calibration curve.

The rate of inhibition was obtained in accordance with the equation shown at (1) above.

B. Test Results

Table 20 shows the rates of inhibition determined for the various gynosaponins as hereinabove described against the decomposition by adrenalin of the fat in the fat cells.

TABLE 20

| Additive | Free fatty acid formed by decomposition of fat (μ Eq/g) | Rate of inhibition (%) |
|---|---|---|
| None | 0 | — |
| Adrenalin | 14.1 | 0 |
| Adrenalin + gynosaponin A | 13.4 | 5 |
| Adrenalin + gynosaponin B | 9.1 | 35 |
| Adrenalin + gynosaponin E | 9.4 | 33 |
| Adrenalin + gynosaponin F | 13.4 | 5 |
| Adrenalin + gynosaponin G | 13.8 | 2 |
| Adrenalin + gynosaponin I | 12.7 | 10 |
| Adrenalin + gynosaponin J | 13.1 | 7 |
| Adrenalin + gynosaponin K | 13.8 | 2 |
| Adrenalin + gynosaponin M | 13.5 | 4 |
| Adrenalin + gynosaponin N | 13.3 | 6 |
| Adrenalin + gynosaponin O | 13.9 | 1 |
| Adrenalin + gynosaponin P | 12.7 | 10 |
| Adrenalin + gynosaponin Q | 13.5 | 4 |
| Adrenalin + gynosaponin R | 14.0 | 1 |
| Adrenalin + gynosaponin S | 13.5 | 4 |
| Adrenalin + gynosaponin T | 13.1 | 7 |
| Adrenalin + gynosaponin U | 13.8 | 2 |
| Adrenalin + progynosapogenin $A_2$ | 13.0 | 8 |
| Adrenalin + progynosapogenin A—AH | 12.4 | 12 |
| Adrenalin + progynosapogenin $O_1$ | 12.6 | 11 |

[Note]
Adrenalin was used in the amount of 1 μg/ml., and the saponins in the amount of 20 μg/ml., in all cases where they were involved.

As is noted from the table, a free fatty acid in the amount of 14.1 μ Eq/g resulted from the decomposition of fat when the fat cells had been acted upon with adrenalin in the amount of 1 μg/ml., and left to stand at 37° C. for two hours, and the use of the gynosaponins each in the amount of 20 μg/ml. restricted the decomposition of fat by adrenalin, thereby reducing the amount of the free fatty acid formed. However, all the gynosaponins tested, except gynosaponins B and E, showed a lower rate of inhibition against the decomposition of fat by adrenalin than against the decomposition of fat by ACTH.

(3) Effects of Gynosaponins on the Synthesis of Fat from Glucose in Fat Cells

A. Test Method $^{14}$C-glucose having its carbon atoms marked with radioactivity was reacted upon fat cells, and a Geiger count was read to determine the amount of the glucose participating in the fat synthesis and incorporated into the fat cells as a neutral fat, whereby gynosaponins were tested for their effects on the power of the glucose for fat synthesis.

More specifically, the fat cells obtained by treating with collagenase were suspended in KRB, and 0.35 ml. of the resulting solution containing 100 mg of fat cells was placed into a test tube with 0.1 ml. of each saponin solution containing 20 μg of saponin, 0.5 ml. of a 5% albumin solution in KRB, containing 10 mM glucose and having a pH value of 7.4, and 0.05 ml. of a $^{14}C$-glucose solution which was a 0.5 μCi KRP solution having a pH value of 7.4 and containing 10 mM glucose. They were heated at 37° C. for half an hour, and after 5 ml. of Dole's extract were added and the whole was shaked for five minutes, 3 ml. of heptane and 2 ml. of water were added, and the whole was shaked for five minutes. 3 ml. of a heptane layer were separated, and after an alkaline ethanol solution (0.5 N sodium hydroxide solution, 50% ethanol solution) was added in the amount of 3 ml., the whole was shaked for five minutes. Then, 1 ml. of an ethanol layer was separated, and 10 ml. of a toluene scintillation solution were added thereinto, followed by determination according to the method of Skipski et al. [Biochem. Biophys. Acta, 106, 386 (1965)].

B. Test Results

Table 21 shows the rates of promotion shown by the gynosaponins on the synthesis of fats from glucose in the fat cells.

TABLE 21

| Additive | Power for Symthesis of neutral fat from glucose (cpm/g) | Rate of promotion (%) |
|---|---|---|
| None | 21,500 | 100 |
| Gynosaponin A (20 μg/ml) | 8,013 | 37 |
| Gynosaponin B (20 μg/ml) | 12,308 | 57 |
| Gynosaponin E (20 μg/ml) | 10,248 | 48 |
| Gynosaponin F (20 μg/ml) | 11,620 | 54 |
| Gynosaponin G (20 μg/ml) | 8,925 | 42 |
| Gynosaponin I (20 μg/ml) | 10,564 | 49 |
| Gynosaponin J (20 μg/ml) | 11,650 | 54 |
| Gynosaponin K (20 μg/ml) | 13,600 | 63 |
| Gynosaponin M (20 μg/ml) | 12,650 | 59 |
| Gynosaponin N (20 μg/ml) | 9,870 | 46 |
| Gynosaponin O (20 μg/ml) | 8,263 | 38 |
| Gynosaponin P (20 μg/ml) | 8,165 | 38 |
| Gynosaponin Q (20 μg/ml) | 11,620 | 54 |
| Gynosaponin R (20 μg/ml) | 12,600 | 59 |
| Gynosaponin S (20 μg/ml) | 10,100 | 47 |
| Gynosaponin T (20 μg/ml) | 11,150 | 52 |
| Gynosaponin U (20 μg/ml) | 13,100 | 61 |
| Progynosapogenin A$_2$ (20 μg/ml) | 12,650 | 59 |
| Progynosapogenin A—AH (20 μg/ml) | 10,550 | 49 |
| Progynosapogenin O$_1$ (20 μg/ml) | 11,200 | 52 |

As is noted from the table, many of the gynosaponins tested showed a reduction in the amount of the glucose incorporated into the fat cells as a neutral fat, to less than a half of the result obtained when no gynosaponin was used. Thus, it is clear that the gynosaponins have a function of inhibiting the synthesis of fat from glucose in the fat cells.

As is obvious from the foregoing description, the gynosaponins of this invention can effectively inhibit both the decomposition and synthesis of fats in the fat cells, and provide, therefore, a new and useful agent for the lipid metabolism.

What we claim is:

1. A compound of the formula (I):

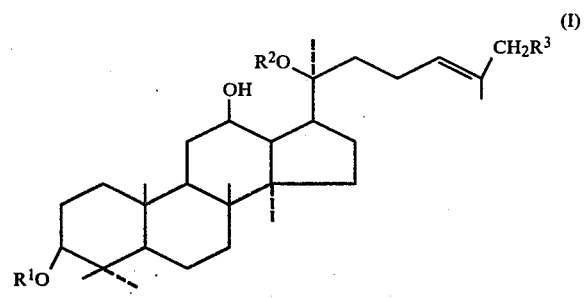

wherein (a) when $R^1$ is [β-D-glucopyranosyl (1→2)-α-L-rhamnopyranosyl (1→6)]-β-D-glucopyranosyl group, $R^2$ is hydrogen, β-D-glucopyranosyl (1→6)-β-D-glucopyranosyl group, α-L-rhamnopyranosyl (1→6)-β-D-glucopyranosyl group or β-D-glucopyranosyl group and $R^3$ is hydrogen atom or hydroxy group;

(b) when $R^1$ is β-D-glucopyranosyl (1→2)-β-D-glucopyranosyl group, $R^2$ is α-L-rhamnopyranosyl (1→6)-β-D-glucopyranosyl group, and $R^3$ is hydrogen atom or hydroxy group;

(c) when $R^1$ is α-L-rhamnopyranosyl (1→6)-β-D-glucopyranosyl group, $R^2$ is β-D-glucopyranosyl (1→6)-β-D-glucopyranosyl group, α-L-rhamnopyranosyl (1→6)-β-D-glucopyranosyl or β-D-glucopyranosyl group and $R^3$ is hydrogen atom;

(d) when $R^1$ is D-glucopyranosyl group, $R^2$ is β-D-xylopyranosyl (1→6)-β-D-glucopyranosyl, α-L-rhamnopyranosyl (1→6)-β-D-glucopyranosyl or β-D-glucopyranosyl (1→6)-β-D-glucopyranosyl group and $R^3$ is hydrogen atom;

(e) when $R^1$ is hydrogen atom, $R^2$ is β-D-glucopyranosyl, β-D-xylopyranosyl (1→6)-β-D-glucopyranosyl or α-L-rhamnopyranosyl (1→6)-β-D-glucopyranosyl group and $R^3$ is hydrogen atom or hydroxy group; except the case where $R_1$ and $R_3$ are hydrogen atom and $R_2$ is β-D-glucopyranosyl group;

(f) when $R^1$ is β-D-xylopyranosyl (1→2)-β-D-glucopyranosyl group, $R^2$ is β-D-xylopyranosyl (1→6)-β-D-glucopyranosyl or α-L-rhamnopyranosyl (1→6)-β-D-glucopyranosyl group and $R^3$ is hydrogen atom, or non-toxic salt thereof.

2. A process for isolating saponins comprising extracting Gynostemma pentaphyllum Makino or botanically similar plant thereto which belongs to Cucurbitaceae, with water or an aqueous lower aliphatic alcohol, treating the resulting extract with a non-ionic adsorption resin, eluting the adsorbed substance with a lower aliphatic alcohol, treating the eluate with an almina, eluting the adsorbed substance with a lower aliphatic alcohol or an aqueous lower aliphatic alcohol to yield saponins substantially free from other components of the plant.

3. The process of claim 2, wherein the saponins are further treated with a styrene adsorption resin or a silica gel to isolate an individual saponin.

4. The process of claim 2 wherein the lower aliphatic alcohol is methanol or ethanol.

5. The process of claim 2 wherein the non-ionic adsorption resin is a high porous styrene-divinylbenene copolymer.

6. The process of claim 3 wherein the treatment of the saponins with styrene adsorption resin includes a gradient elution with 20–99% methanol.

7. The process of either claim 3 or 6, wherein the eluated fractions of 30–40% methanol is treated with a silica gel followed by elution with a solvent system of chloroform, a lower aliphatic alcohol and water, to yield a gynosaponin selected from the group consisting of 20S,26-Hydroxyprotopanaxadiol-3-O-[β-D-glucopyranosyl (1→2)-β-D-glucopyranoside]-20-O-[α-L-rhamnopyranosyl (1→6)-β-D-glucopyranoside]... "gynosaponin P"

20S,26-Hydroxyprotopanaxadiol-3-O-{[β-D-glucopyranosyl (1→2)-α-L-rhamnopyranosyl (1→6)]-β-D-glucopyranoside{-20-O-[α-L-rhamnopyranosyl (1→6)-β-D-glucopyranoside]. . . "gynosaponin O" and 20S,26-Hydroxprotopanaxadiol-3-O-{[β-D-glucopyranosyl (1→2)-α-L-rhamnopyranosyl (1→6)]-β-D-glucopyranoside}-20-O-[β-D-glucopyranosyl (1→6)-β-D-glucopyranoside]. . . "gynosaponin T".

8. The process of either claim 3 or 6 wherein the eluated fractions of 45–99% methanol are treated with a silica gel followed by elution with a solvent system of chloroform, a lower aliphatic alcohol and water, to yield a gynosaponin selected from the group consisting of 20S-Protopanaxadiol-3-O-{[β-D-glucopyranosyl (1→2)-α-L-rhamnopyranosyl (1→6)]-β-D-glucopyranoside}-20-O-[β-D-glucopyranosyl (1→6)-β-D-glucopyranoside]-; "gynosaponin A"

20S-Protopanaxadiol-3-O-{[β-D-glucopyranosyl (1→2)-α-L-rhamnopyranosyl (1→6)]-β-D-glucopyranoside}-20-O-[α-L-rhamnopyranosyl (1→6)-β-D-glucopyranoside]. . . "gynosaponin B"

20S-Protopanaxadiol-3-O-[β-D-glucopyranosyl (1→2)-β-D-glucopyranoside]-20-O-[β-D-glucopyranosyl (1→6)-β-D-glucopyranoside]. . . "gynosaponin C"

20S-Protopanaxadiol-3-O-[β-D-glucopyranosyl (1→2)-β-D-glucopyranoside]-20-O-[β-D-xylopyranosyl (1→6)-β-D-glucopyranoside]. . . "gynosaponin D"

20S-protopanaxadiol-3-O-[β-D-glucopyranosyl (1→2)-β-D-glucopyranoside]-20-O-β-D-glucopyranoside . . . "gynosaponin H"

20S-Protopanaxadiol-3,20-di(O-β-D-glucopyranoside) . . . "gynosaponin L"

20S-Protopanaxadiol-3-O-{[β-D-glucopyranosyl (1→2)-α-L-rhamnopyranosyl (1→6)]-β-D-glucopyranoside}-20-O-β-D-glucopyranoside . . . "gynosaponin F"

20S-Protopanaxadiol-3-O-[β-D-glucopyranosyl (1→2)-β-D-glucopyranoside]-20-O-[α-L-rhamnopyranosyl (1→6)-β-D-glucopyranoside]. . . "gynosaponin E"

20S-Protopanaxadiol-3,20-bis-O-[α-L-rhamnopyranosyl (1→6)-β-D-glucopyranoside]. . . "gynosaponin G"

20S-Protopanaxadiol-3-O-[α-L-rhamnopyranosyl (1→6)-βD-glucopyranoside]-20-O-β-D-glucopyranoside . . . "gynosaponin K"

20S-Protopanaxadiol-3-O-β-D-glucopyranoside -20-O-[β-D-xylopyranosyl (1→6)-β-D-glucopyranoside]. . . "gynosaponin I"

20S-Protopanaxadiol-3-O-β-D-glucopyranoside-20-O-[α-L-rhamnopyranosyl (1→6)-β-D-glucopyranoside]. . . "gynosaponin J"

20S-Protopanaxadiol-20-O-[β-D-xylopyranosyl (1→6)-β-D-glucopyranoside]. . . "gynosaponin M"

20S-Protopanaxadiol-20-O-[α-L-rhamnopyranosyl (1→6)-β-D-glucopyranoside]. . . "gynosaponin N"

20S-Protopanaxadiol-3-O-[β-D-xylopyranosyl (1→2)-β-D-glucopyranoside]-20-O-[β-D-xylopyranosyl (1→6)-β-D-glucopyranoside]. . . "gynosaponin Q"

20S-Protopanaxadiol-3-O-[β-D-xylopyranosyl (1→2)-β-D-glucopyranoside]-20-O-[α-L-rhamnopyranosyl (1→6)-β-D-glucopyranoside]. . . "gynosaponin R"

20S-Protopanaxadiol-3-O-β-D-glucopyranoside -20-O-[β-D-glucopyranosyl (1→6)-β-D-glucopyranoside]. . . "gynosaponin S" and 20S,26-Hydroxyprotopanaxadiol-20-O-[β-D-xylopyranosyl (1→6)-β-D-glucopyranoside]. . . "gynosaponin U".

9. A process of any of claims 3, 4, 5 or 6, wherein Gynostemma pentaphyllum Makino is used as the raw material.

10. A process for preparing saponins which comprises hydrolyzing a compound of the formula (I) as defined in claim 1 or the formula (II)

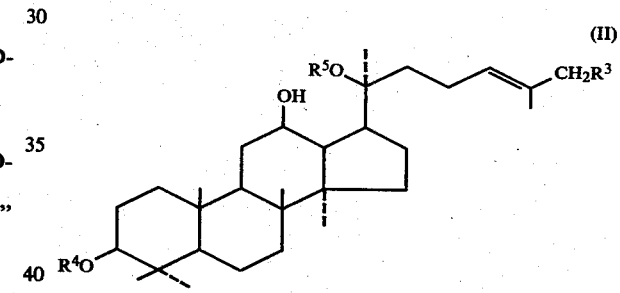

(II)

wherein R⁴ is β-D-glucopyranosyl (1→2)-β-D-glucopyranosyl group, and R⁵ is β-D-glucopyranosyl (1→6)-β-D-glucopyranosyl group, β-D-xylopyranosyl (1→6)-β-D-glucopyranosyl group or β-D-glucopyranosyl group, or R⁴ is β-D-glucopyranosyl group and R⁵ is β-D-glucopyranosyl group, with an enzyme, to remove at least one carbohydrate moiety from the substituents at the 3rd and/or 20th positions.

11. The process of claim 10 wherein the enzyme is hesperidinase, maltase, cellulase or takadiastase.

12. The process of claim 11 wherein the enzyme is cellulase.

13. A process for preparing saponins which comprises hydrolyzing a compound of the formula (I) as defined in claim 1 or the formula (II) as defined in claim 10, with a weak acid, to remove a carbohydrate moiety at the 20th substituent.

14. The process of claim 13 wherein the weak acid is acetic acid.

15. The process of claim 14 wherein acetic acid is used as 40–60% acetic acid aqueous solution.

16. A pharmaceutical composition which comprises a therapeutically effective amount of a saponin isolated from Gynostemma pentaphyllum Makino or botanically similar plant thereto which belongs to Cucurbitaceae and a pharmaceutically acceptable carrier.

17. A composition according to claim 16, wherein the saponin contains at least one compound of the formula (I) as defined in claim 1.

18. A composition according to claim 16, wherein the saponin contains at least one compound of the formula I as defined in claim 1 and at least one compound of the formula II as defined in claim 10.

19. A composition according to any of claims 16, 17 or 18, wherein one part of said saponin is used for every nine parts of said pharmaceutically acceptable carrier.

20. A composition according to claim 19, wherein said pharmaceutically acceptable carrier is lactose.

21. A method for treating an ulcer which comprises administering to a host afflicted with said ulcer a therapeutically effective amount of a saponin isolated from *Gynostemma pentaphyllum Makino* or a botanically similar plant thereto which belongs to Cucurbitaceae and a pharmaceutically acceptable carrier.

22. The method according to claim 21, wherein said therapeutically effective amount is of from about 50 to about 1,000 mg per day in two or three doses.

23. The method according to claim 22, wherein said therapeutically effective amount is 100 to 200 mg per day in two or three doses.

24. A method according to either claim 21 or 22, wherein one part of the saponin is used for every nine parts of the pharmaceutically acceptable carrier.

25. A method according to claim 21, wherein said pharmaceutically acceptable carrier is lactose.

26. A method of treating adrenal atrophy comprising administering to a host afflicted with adrenal atrophy a therapeutically effective amount of a saponin isolated from *Gynostemma pentaphyllum Makino* or a botanically similar plant thereto which belongs to Cucurbitaceae together with a pharmaceutically acceptable carrier.

27. A method according to claim 26, wherein said therapeutically effective amount is of from about 5 to about 500 mg per day in three or four doses.

28. A method according to claim 27, wherein said therapeutically effective amount is of from about 10 to about 250 mg per day in three or four doses.

29. A method of treating adrenal atrophy comprising administering to a host afflicted with adrenal atrophy a therapeutically effective amount of a composition comprising a saponin isolated from *Gynostemma pentaphyllum Makino* or a botanically similar plant thereto which belongs to Cucurbitaceae, a glucocorticoid and a pharmaceutically acceptable carrier.

30. The method according to claim 29, wherein said composition is administered in the form of an oral preparation wherein from about 5 to about 100 mg of the saponin and from about 0.5 to about 10 mg of the glucocorticoid per gram are contained.

31. The method according to claim 29, wherein said composition is used in the form of an external preparation wherein from about 0.1 to about 10% (W/V) of the saponin component and from about 0.05 to about 1% (W/V) of the glucocorticoid are contained.

32. A method according to claim 29, wherein said composition is used in the form for an injection administration wherein from about 5 to about 50 mg of the saponin component and from about 1 to about 20 mg of the glucocorticoid are contained per milliliter.

33. A pharmaceutical composition comprising, as the active ingredient, a therapeutically effective amount of a saponin isolated from *Gynostemma pentaphyllum Makino* or botanically similar plant thereto which belongs to Cucurbitaceae and a glucocorticoid.

34. A composition of claim 33 which additionally comprises a pharmaceutically acceptable carrier.

35. A pharmaceutical composition according to either claim 33 or 34, which is in the form of an oral preparation wherein from about 5 to about 100 mgs of the saponin and from about 0.5 to about 10 mgs of the glucocorticoid per gram are contained.

36. The pharmaceutical composition according to either claim 33 or 34, which is in the form of an external preparation wherein from about 0.1 to about 10% (W/V) of the saponin component and from about 0.05 to about 1% (W/V) of the glucocorticoid are contained.

37. The pharmaceutical composition according to either claim 33 or 34, which is in the form of an injection administration wherein from about 5 to about 50 mgs of the saponin component and from about 1 to about 20 mgs of the glucocorticoid are contained per milliliter.

38. The pharmaceutical composition according to either claim 33 or 34, wherein said glucocorticoid is selected from the group consisting of dexamethasone and prednisolone.

39. The pharmaceutical composition according to either claim 33 or 34, wherein the saponin contains at least one compound of the formula I as defined in claim 1.

40. The pharmaceutical composition according to either claim 33 or 34, wherein the saponin contains at least one compound of the formula I as defined in claim 1 and at least one compound of the formula II as defined in claim 10.

41. The method according to claim 21, wherein the saponin contains at least one compound of the formula I as defined in claim 1.

42. The method according to claim 21, wherein the saponin contains at least one compound of the formula I as defined in claim 1 and at least one compound of the formula II as defined in claim 10.

43. A method for activating a body cell in a host so as to prevent aging of the cell which comprises administering to a host a saponin isolated from *Gynostemma pentaphyllum Makino* or a botanically similar plant thereto which belongs to Cucurbitaceae together with a pharmaceutically acceptable carrier.

44. A method for preventing fatigue which comprises administering to a host a therapeutically effective amount of a saponin isolated from *Gynostemma pentaphyllum Makino* or a botanically similar plant thereto which belongs to Cucurbitaceae together with a pharmaceutically acceptable carrier.

45. A method for sedating a host which comprises administering to a host a therapeutically effective amount of a saponin isolated from *Gynostemma pentaphyllum Makino* or a botanically similar plant thereto which belongs to Cucurbitaceae together with a pharmaceutically acceptable carrier.

46. A method according to any of claim 41, 42 or 43, wherein said therapeutically effective amount is from about 20 to about 500 mg per day in two or three doses every day.

47. A method according to claim 44, wherein said therapeutically effective amount is from about 50 to about 300 mg per day in two or three doses every day.

48. A method for promoting lipid metabolism in a host which comprises administering to the host a therapeutically effective amount of a saponin isolated from *Gynostemma pentaphyllum Makino* or a botanically similar plant thereto which belongs to Cucurbitaceae together with a pharmaceutically acceptable carrier.

49. The method according to either claims 43, 44, 45 or 48, wherein the saponin contains at least one compound of the formula I as defined in claim 1.

50. The method according to any of claims 43, 44, 45 or 48, wherein the saponin contains at least one compound of the formula I as defined in claim 1 and at least one compound of the formula II as defined in claim 10.

51. The compound according to claim 1, wherein said compound of formula I is
20S-Protopanaxadiol-3-O-{[β-D-glucopyranosyl (1→2)-α-L-rhamnopyranosyl (1→6)]-β-D-glucopyranoside}-20-O-[β-D-glucopyranosyl (1→6)-β-D-glucopyranoside]-; "gynosaponin A?.

52. The compound according to claim 1, wherein said compound of formula I is
20S-Protopanaxadiol-3-O-{[β-D-glucopyranosyl (1→2)-α-L-rhamnopyranosyl (1→6)]-β-D-glucopyranoside}-20-O-[α-L-rhamnopyranosyl (1→6)-β-D-glucopyranoside]... "gynosaponin B".

53. The compound according to claim 1, wherein said compound of formula I is
20S-Protopanaxadiol-3-O-[β-D-glucopyranosyl (1→2)-β-D-glucopyranoside]-20-O-[α-L-rhamnopyranosyl (1→6)-β-D-glucopyranoside]... "gynosaponin E".

54. The compound according to claim 1, wherein said compound of formula I is
20S-Protopanaxadiol-3-O-{[β-D-glucopyranosyl (1→2)-α-L-rhamnopyranosyl (1→6)]-β-D-glucopyranoside}-20-O-β-D-glucopyranoside ... "gynosaponin F".

55. The compound according to claim 1, wherein said compound of formula I is
20S-Protopanaxadiol-3,20-bis-O-[α-L-rhamnopyranosyl (1→6)-β-D-glucopyranoside]... "gynosaponin G".

56. The compound according to claim 1, wherein said compound of formula I is
20S-Protopanaxadiol-3-O-β-D-glucopyranoside -20-O-[β-D-xylopyranosyl (1→6)-β-D-glucopyranoside]... "gynosaponin I".

57. The compound according to claim 1, wherein said compound of formula I is
20S-Protopanaxadiol-3-O-β-D-glucopyranoside-20-O-[α-L-rhamnopyranosyl (1→6)-β-D-glucopyranoside]... "gynosaponin J".

58. The compound according to claim 1, wherein said compound of formula I is
20S-Protopanaxadiol-3-O-[α-L-rhamnopyranosyl (1→6)-β-D-glucopyranoside]-20-O-β-D-glucopyranoside ... "gynosaponin K".

59. The compound according to claim 1, wherein said compound of formula I is
20S-Protopanaxadiol-20-O-[β-D-xylopyranosyl (1→6)-β-D-glucopyranoside]... "gynosaponin M".

60. The compound according to claim 1, wherein said compound of formula I is
20S-Protopanaxadiol-20-O-[α-L-rhamnopyranosyl (1→6)-β-D-glucopyranoside]... "gynosaponin N".

61. The compound according to claim 1, wherein said compound of formula I is
20S,26-Hydroxyprotopanaxadiol-3-O-{[β-D-glucopyranosyl (1→2)-α-L-rhamnopyranosyl (1→6)]-β-D-glucopyranoside}-20-O-[α-L-rhamnopyranosyl (1→6)-β-D-glucopyranoside]... "gynosaponin O".

62. The compound according to claim 1, wherein said compound of formula I is
20S,26-Hydroxyprotopanaxadiol-3-O-[β-D-glucopyranosyl (1→2)-β-D-glucopyranoside]-20-O-[α-L-rhamnopyranosyl (1→6)-β-D-glucopyranoside]... "gynosaponin P".

63. The compound according to claim 1, wherein said compound of formula I is
20S-Protopanaxadiol-3-O-[β-D-xylopyranosyl (1→2)-β-D-glucopyranoside]-20-O-[β-D-xylopyranosyl (1→6)-β-D-glucopyranoside]... "gynosaponin Q".

64. The compound according to claim 1, wherein said compound of formula I is
20S-Protopanaxadiol-3-O[β-D-xylopyranosyl (1→2)-β-D-glucopyranoside]-20-O-[α-L-rhamnopyranosyl (1→6)-β-D-glucopyranoside]... "gynosaponin R".

65. The compound according to claim 1, wherein said compound of formula I is
20S-Protopanaxadiol-3-O-β-D-glucopyranoside -20-O-[β-D-glucopyranosyl (1→6)-β-D-glucopyranoside]... "gynosaponin S".

66. The compound according to claim 1, wherein said compound of formula I is
20S,26-Hydroxyprotopanaxadiol-3-O-{[β-D-glucopyranosyl (1→2)-α-L-rhamnopyranosyl (1→6)]-β-D-glucopyranoside}-20-O-[β-D-glucopyranosyl (1→6)-β-D-glucopyranoside]... "gynosaponin T".

67. The compound according to claim 1, wherein said compound of formula I is
20S,26-Hydroxyprotopanaxadiol-20-O-[β-D-xylopyranosyl (1→6)-β-D-glucopyranoside]... "gynosaponin U".

68. The compound according to claim 1, wherein said compound of formula I is
20S-Protopanaxadiol-3-O-[α-L-rhamnopyranosyl (1→6)-β-D-glucopyranoside]-20-O-[β-D-glucopyranosyl (1→6)-β-D-glucopyranoside]... "progynosapogenin $A_2$".

69. The compound according to claim 1, wherein said compound of formula I is
20S-Protopanaxadiol-3-O-{[β-D-glucopyranosyl (1→2) -α-L-rhamnopyranosyl (1→6)]-β-D-glucopyranoside}... "progynosapogenin A-AH".

70. The compound according to claim 1, wherein said compound of formula I is
20S,26-Hydroxyprotopanaxadiol-20-O-β-D-glucopyranoside ... "progynosapogenin $O_1$".

* * * * *